(12) United States Patent
Chang et al.

(10) Patent No.: US 8,501,957 B2
(45) Date of Patent: Aug. 6, 2013

(54) BENZIMIDAZOLE COMPOUNDS AND THEIR USE AS ANTICANCER AGENTS

(75) Inventors: Chih-Shiang Chang, Taichung (TW); Jih-Hwa Guh, Taipei (TW); Che-Ming Teng, Taipei (TW); Shiow-Lin Pan, Taipei (TW); Wei-Ling Chang, Taipei (TW); Ju-Fang Liu, Taichung (TW); Kai-Wei Chang, Taichung (TW); Sheng-Chu Kuo, Taichung (TW)

(73) Assignee: China Medical University, Taichung (TW)

( * ) Notice: Subject to any disclaimer, the term of this patent is extended or adjusted under 35 U.S.C. 154(b) by 364 days.

(21) Appl. No.: 12/635,206

(22) Filed: Dec. 10, 2009

(65) Prior Publication Data
US 2010/0179147 A1    Jul. 15, 2010

Related U.S. Application Data

(60) Provisional application No. 61/121,372, filed on Dec. 10, 2008.

(51) Int. Cl.
*A61K 31/4184* (2006.01)
*C07D 235/18* (2006.01)

(52) U.S. Cl.
USPC .......... 548/310.7; 548/305.1; 548/304.7; 548/310.4; 514/394

(58) Field of Classification Search
USPC .......................................... 548/310.7
See application file for complete search history.

(56) References Cited

U.S. PATENT DOCUMENTS

| | | | | |
|---|---|---|---|---|
| 2,876,233 A | * | 3/1959 | Herrling et al. | 548/304.4 |
| 3,192,227 A | * | 6/1965 | Brown et al. | 548/309.4 |
| 3,336,192 A | * | 8/1967 | Brown et al. | 514/365 |
| 3,586,694 A | * | 6/1971 | Shen et al. | 548/309.4 |
| 3,625,954 A | * | 12/1971 | Sarges | 548/309.4 |
| 5,552,426 A | * | 9/1996 | Lunn et al. | 514/394 |
| 5,654,436 A | * | 8/1997 | Elokdah et al. | 546/273.4 |
| 6,211,177 B1 | * | 4/2001 | Sperl et al. | 514/241 |
| 6,348,032 B1 | * | 2/2002 | Sperl et al. | 514/338 |
| 6,352,985 B1 | * | 3/2002 | Yamasaki et al. | 514/227.8 |
| 6,452,014 B1 | * | 9/2002 | Akama et al. | 546/260 |
| 2007/0004713 A1 | * | 1/2007 | Barlaam et al. | 514/227.8 |

FOREIGN PATENT DOCUMENTS

| JP | 49/76870 A | * | 7/1974 |
|---|---|---|---|
| WO | WO-2006/039215 A2 | * | 4/2006 |

OTHER PUBLICATIONS

Rao et al., CA 52:6353, 1958.*
Chang et al., CA 145:210949, 2005.*
Golub et al., Science, vol. 286, Oct. 15, 1999, pp. 531-537.*
Inoue et al., CA 82:16840, 1975.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Vitale et al.; "Combretastatin CA-4 and combretastatin derivative induce mitotic catastrophe dependent on spindle checkpoint and caspase-3 activation in non-small cell lung cancer cells"; Apoptosis, 12:155-166 (2007).
Critchley et al.; "Albendazole for lymphatic filariasis (Review)"; The Cochrane Collaboration, Issue 1 p. 1-58 (2009).

* cited by examiner

*Primary Examiner* — Laura L. Stockton
(74) *Attorney, Agent, or Firm* — Occhiuti Rohlicek & Tsao LLP

(57) ABSTRACT

Benzimidazole compounds of formula (I):

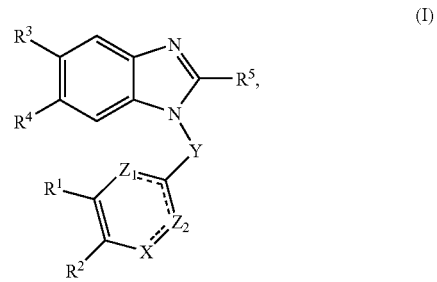

wherein $R^1, R^2, R^3, R^4, R^5, X, Y, Z_1$, and $Z_2$ are defined herein. Also disclosed is a method for treating cancer with benzimidazole compounds.

13 Claims, No Drawings

BENZIMIDAZOLE COMPOUNDS AND THEIR USE AS ANTICANCER AGENTS

CROSS-REFERENCE TO RELATED APPLICATIONS

This application claims priority to U.S. Provisional Application No. 61/121,372, filed on Dec. 10, 2008, the content of which is hereby incorporated by reference in its entirety.

BACKGROUND

Microtubules are intracellular tubes composed of α- and β-tubulins. As important components of cytoskeleton, they play important roles in, among others, cell division, which is essential to cancer development. Thus, microtubules/tubulins have attracted great attention as targets of cancer therapy.

DNA is another therapeutic target for treating cancer. It is known that DNA damage induces cell death via apoptosis. Agents that induce DNA damage can therefore serve as anticancer drugs.

SUMMARY

This invention is based on the unexpected discovery that certain benzimidazole compounds have potent anticancer activity. Thus, this invention relates to benzimidazole compounds and their use in cancer treatment.

In one aspect, this invention features a benzimidazole compound of formula (I):

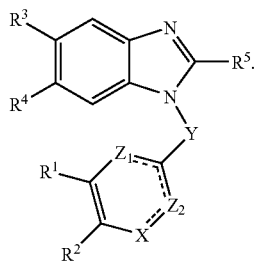

(I)

In formula (I), each ----- is a single bond or a double bond, provided that if one ----- is a double bond, its neighboring ----- is not a double bond; X is CR', NR", N, O, or S, in which R' is H, alkyl, hydroxy, alkoxy, cycloalkyl, heterocycloalkyl, aryl, or heteroaryl, and R" is arylsulfonyl; Y is (CH$_2$)$_n$ in which n is 1, 2, 3, or 4, C(O), SO, SO$_2$, or NR''' in which R''' is H or alkyl; each of Z$_1$ and Z$_2$ is CH or deleted, provided that at most one of Z$_1$ and Z$_2$ is deleted; each of R$^1$ and R$^2$, independently, is H, halo, alkyl, hydroxy, alkoxy, cycloalkyl, heterocycloalkyl, aryl, or heteroaryl; or R$_1$ and R$_2$ together with the C atoms to which they are attached are aryl or heteroaryl; each of R$^3$ and R$^4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, SR$_a$, C(O)R$_a$, or C(O)OR$_a$, in which R$_a$ is H, alkyl, alkenyl, alkynyl, cycloalkyl, cycloalkenyl, heterocycloalkyl, heterocycloalkenyl, aryl, or heteroaryl, provided that at most one of R$^3$ and R$^4$ is H; and R$^5$ is alkyl, alkenyl, alkynyl, cycloalkyl, cycloalkenyl, heterocycloalkyl, heterocycloalkenyl, aryl, and heteroaryl.

One subset of the above-described benzimidazole compounds includes those in which Y is CH$_2$. In these compounds, X can be CR', and each of Z$_1$ and Z$_2$ can be CH; X can be NR", and one of Z$_1$ and Z$_2$ can be CH and the other can be deleted; X can be N, and Z$_1$ and Z$_2$ can be CH; each of R', R$^1$, and R$^2$ can be alkoxy (e.g., methoxy); one of R$^3$ and R$^4$ can be H and the other can be alkyl, halo, alkoxy, cycloalkyl, heterocycloalkyl, aryl, or heteroaryl; R$^5$ can be cycloalkyl, heterocycloalkyl, aryl (e.g., phenyl), or heteroaryl (e.g., furyl or thiophenyl); or R$_1$ and R$_2$ together with the C atoms to which they are attached can be aryl.

Another subset of the above-described benzimidazole compounds includes those in which Y is CO. In these compounds, X can be CR', and Z$_1$ and Z$_2$ can be CH; X can be O or S, and one of Z$_1$ and Z$_2$ can be CH and the other can be deleted; or R$^5$ can be alkyl or aryl.

Still another subset of the above-described benzimidazole compounds includes those in which Y is SO$_2$.

The term "alkyl" refers to a straight or branched monovalent hydrocarbon containing, unless otherwise stated, 1-20 carbon atoms (e.g., C$_1$-C$_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., C$_2$-C$_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., C$_2$-C$_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to NH$_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The terms "amido" and "carbamido" refer to —NRC(O)R' and —C(O)NRR' radicals respectively, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., C$_3$-C$_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantyl. The term "cycloalkenyl" refers to a monovalent non-aromatic hydrocarbon ring system having 3 to 30 carbons (e.g., C$_3$-C$_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "arylsulfonyl" refers to a —SO$_2$-aryl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, amino, aryl, and heteroaryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, alkylthio, arylthio, alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The benzimidazole compounds described herein include the compounds themselves, as well as their salts, their solvates, and their prodrugs, if applicable. A salt, for example, can be formed between an anion and a positively charged group (e.g., amino) on a benzimidazole compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a benzimidazole compound. Suitable cations include sodium ion, potassium ion, magnesium ion, calcium ion, and an ammonium cation such as tetramethylammonium ion. The benzimidazole compounds also include those salts containing quaternary nitrogen atoms. Examples of prodrugs include esters and other pharmaceutically acceptable derivatives, which, upon administration to a subject, are capable of providing active benzimidazole compounds.

In another aspect, this invention relates to a method for treating cancer by administering to a subject in need thereof an effective amount of a benzimidazole compound of formula (I):

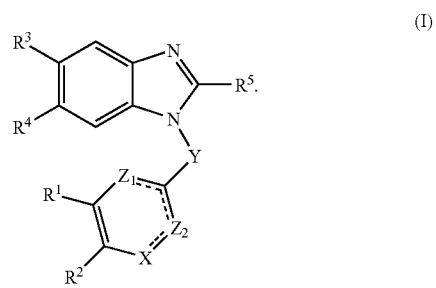

In this formula, each ---- is a single bond or a double bond, provided that if one ---- is a double bond, its neighboring ---- is not a double bond; X is CR', NR", N, O, or S, in which R' is H, alkyl, hydroxy, alkoxy, cycloalkyl, heterocycloalkyl, aryl, or heteroaryl, and R" is arylsulfonyl; Y is (CH$_2$) in which n is 1, 2, 3, or 4, C(O), SO, SO$_2$, or NR'" in which R'" is H or alkyl; each of $Z_1$ and $Z_2$ is CH or deleted, provided that at most one of $Z_1$ and $Z_2$ is deleted; each of $R^1$ and $R^2$, independently, is H, halo, alkyl, hydroxy, alkoxy, cycloalkyl, heterocycloalkyl, aryl, or heteroaryl; or $R_1$ and $R_2$ together with the C atoms to which they are attached are aryl or heteroaryl; each of $R^3$ and $R^4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, SR$_a$, C(O)R$_a$, or C(O)OR$_a$, in which R$_a$ is H, alkyl, alkenyl, alkynyl, cycloalkyl, cycloalkenyl, heterocycloalkyl, heterocycloalkenyl, aryl, or heteroaryl; and $R^5$ is alkyl, alkenyl, alkynyl, cycloalkyl, cycloalkenyl, heterocycloalkyl, heterocycloalkenyl, aryl, and heteroaryl.

Referring to formula (I), a subset of the just-described benzimidazole compounds includes those in which Y is CH$_2$. In these compounds, X can be CR', and each of $Z_1$ and $Z_2$ can be CH; X can be NR", and one of $Z_1$ and $Z_2$ can be CH and the other can be deleted; X can be N, and $Z_1$ and $Z_2$ can be CH; each of R', $R^1$, and $R^2$ can be alkoxy (e.g., methoxy); one of $R^3$ and $R^4$ can be H and the other can be alkyl, halo, alkoxy, cycloalkyl, heterocycloalkyl, aryl, or heteroaryl; $R^5$ can be cycloalkyl, heterocycloalkyl, aryl (e.g., phenyl), or heteroaryl (e.g., furyl or thiophenyl); or $R_1$ and $R_2$ together with the C atoms to which they are attached can be aryl.

Another subset of these benzimidazole compounds includes those in which Y is CO. In these compounds, X can be CR', and $Z_1$ and $Z_2$ can be CH; X can be O or S, and one of $Z_1$ and $Z_2$ can be CH and the other can be deleted; or $R^5$ can be alkyl or aryl.

Still another subset of the compounds of formula (I) includes those in which Y is SO$_2$.

Also within the scope of this invention is a pharmaceutical composition containing one or more of the above-described benzimidazole compounds for use in treating cancer, as well as this therapeutic use and use of the compounds for the manufacture of a medicament for treating cancer.

The details of one or more embodiments of the invention are set forth in the description below. Other features, objects, and advantages of the invention will be apparent from the description and the claims.

DETAILED DESCRIPTION

Shown below are exemplary compounds described herein:

TABLE 1

Compounds

| Compound # | $R_1$ | $R_2$ | $R_3$ | $R_4$ | $R_5$ | $R_6$ | $R_7$ |
|---|---|---|---|---|---|---|---|
| 1 | Cl | H | H | H | H | H | H |
| 2 | Cl | H | H | H | Cl | H | H |
| 3 | Cl | H | H | H | F | H | H |
| 4 | Cl | H | H | H | $OCH_3$ | H | H |
| 5 | $CH_3$ | H | H | H | H | H | H |
| 6 | $CH_3$ | H | H | H | Cl | H | H |
| 7 | $CH_3$ | H | H | H | F | H | H |
| 8 | $CH_3$ | H | H | H | $OCH_3$ | H | H |
| 9 | H | Cl | H | H | H | H | H |
| 10 | H | Cl | H | H | Cl | H | H |
| 11 | H | Cl | H | H | F | H | H |
| 12 | H | Cl | H | H | $OCH_3$ | H | H |
| 13 | H | $CH_3$ | H | H | H | H | H |
| 14 | H | $CH_3$ | H | H | Cl | H | H |
| 15 | H | $CH_3$ | H | H | F | H | H |
| 16 | H | $CH_3$ | H | H | $OCH_3$ | H | H |
| 17 | H | $OCH_3$ | H | H | H | H | H |
| 18 | H | $OCH_3$ | H | H | Cl | H | H |
| 19 | H | $OCH_3$ | H | H | F | H | H |
| 20 | H | $OCH_3$ | H | H | $OCH_3$ | H | H |
| 21 | $CH_3$ | $CH_3$ | H | H | H | H | H |
| 22 | $CH_3$ | $CH_3$ | H | H | Cl | H | H |
| 23 | $CH_3$ | $CH_3$ | H | H | F | H | H |
| 24 | $CH_3$ | $CH_3$ | H | H | $OCH_3$ | H | H |
| 25 | $CH_3$ | H | H | H | $CH_3$ | H | H |
| 26 | $CH_3$ | H | H | $CH_3$ | H | H | H |
| 27 | $CH_3$ | H | $CH_3$ | H | H | H | H |
| 28 | $CH_3$ | H | H | $CH_3$ | $CH_3$ | H | H |
| 29 | $CH_3$ | H | H | F | H | H | H |
| 30 | $CH_3$ | H | F | H | H | H | H |
| 31 | $CH_3$ | H | F | H | F | H | H |
| 32 | $CH_3$ | H | H | F | H | F | H |
| 33 | $CH_3$ | H | H | $OCH_3$ | $OCH_3$ | H | H |
| 34 | $CH_3$ | H | H | $OCH_3$ | H | H | H |
| 35 | $CH_3$ | H | $OCH_3$ | H | H | H | H |
| 36 | $CH_3$ | H | H | $OCH_3$ | H | $OCH_3$ | H |
| 37 | $CH_3$ | H | H | H | CN | H | H |
| 38 | $CH_3$ | H | Cl | Cl | H | H | H |
| 39 | $CH_3$ | H | H | Cl | H | Cl | H |
| 40 | $CH_3$ | H | H | Cl | Cl | H | H |
| 41 | $CH_3$ | H | H | Cl | H | H | H |
| 42 | $CH_3$ | H | Cl | H | Cl | H | H |
| 43 | $CH_3$ | H | F | H | H | H | F |
| 44 | $CH_3$ | H | H | $CF_3$ | H | $CF_3$ | H |
| 45 | $CH_3$ | H | Cl | H | H | H | H |
| 46 | $CH_3$ | H | F | H | H | F | H |
| 47 | $CH_3$ | H | H | $OCH_3$ | $OCH_3$ | $OCH_3$ | H |
| 48 | $CH_3$ | H | $OC_2H_5$ | H | H | H | H |
| 49 | $CH_3$ | H | Cl | H | H | H | Cl |
| 50 | $CH_3$ | H | $CF_3$ | H | H | H | H |
| 51 | $CH_3$ | H | $OCH_3$ | H | H | H | $OCH_3$ |
| 52 | $CH_3$ | H | F | H | H | F | H |
| 53 | $CH_3$ | H | $COCH_3$ | H | H | H | H |
| 54 | $SC_3H_7$ | H | H | H | H | H | H |
| 55 | N-pyrrolidinyl | H | H | H | H | H | H |
| 56 | N-pyrrolidinyl | H | $OCH_3$ | H | H | H | H |

TABLE 1-continued

Compounds

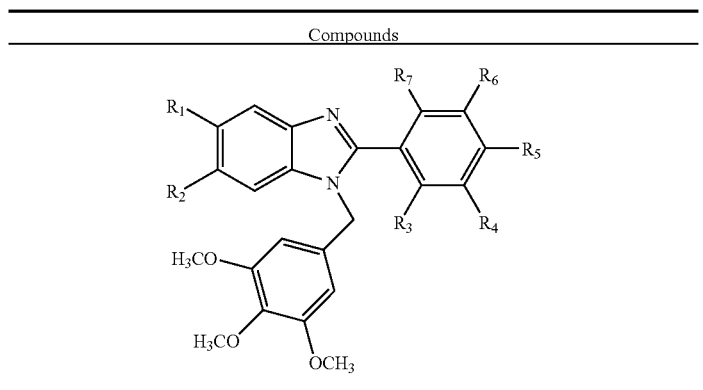

| Compound # | $R_1$ | $R_2$ | $R_3$ | $R_4$ | $R_5$ | $R_6$ | $R_7$ |
|---|---|---|---|---|---|---|---|
| 57 | OCH$_3$ | H | H | H | H | H | H |
| 58 | H | H | H | H | H | H | H |
| 59 | F | H | H | H | H | H | H |
| 60 | H | CN | H | H | H | H | H |
| 61 | H | OH | H | H | H | H | H |
| 62 | H | F | H | H | H | H | H |
| 63 | H | benzoyl | H | H | H | H | H |
| 64 | N-pyrrolidinyl | H | OC$_2$H$_5$ | H | H | H | H |
| 65 | N-pyrrolidinyl | H | OCH$_3$ | H | H | H | H |
| 66 | N-pyrrolidinyl | H | OCH$_3$ | H | H | H | H |
| 67 | N-morpholinyl | H | OCH$_3$ | H | H | H | H |

TABLE 2

Compounds

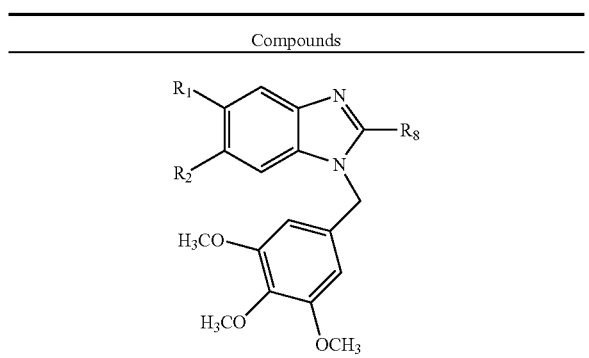

| Compound # | $R_1$ | $R_2$ | $R_8$ |
|---|---|---|---|
| 68 | CH$_3$ | H | cyclohexyl |
| 69 | CH$_3$ | H | thiophen-2-yl |
| 70 | CH$_3$ | H | 4-pyridinyl |
| 71 | CH$_3$ | H | propyl |
| 72 | CH$_3$ | H | adamantyl |
| 73 | CH$_3$ | H | 1-naphthyl |
| 74 | CH$_3$ | H | 2-naphthyl |
| 75 | CH$_3$ | H | benzyl |
| 76 | CH$_3$ | H | styryl |
| 77 | N-pyrrolidinyl | H | 2-furyl |
| 78 | N-pyrrolidinyl | H | thiophen-2-yl |
| 79 | N,N-dimethylamino | H | 2-furyl |
| 80 | N-piperidinyl | H | benzyl |
| 81 | N-piperidinyl | H | 2-furyl |
| 82 | N-methylpiperazinyl | H | benzyl |
| 83 | N-methylpiperazinyl | H | 2-furyl |
| 84 | morpholinyl | H | benzyl |
| 85 | morpholinyl | H | 2-furyl |
| 86 | CH$_3$ | H | 3-pyridinyl |
| 87 | CH$_3$ | H | 2-furyl |

TABLE 3

Compounds

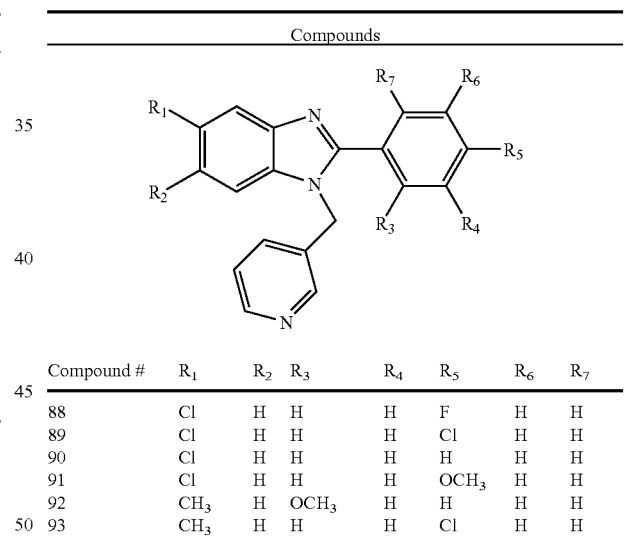

| Compound # | $R_1$ | $R_2$ | $R_3$ | $R_4$ | $R_5$ | $R_6$ | $R_7$ |
|---|---|---|---|---|---|---|---|
| 88 | Cl | H | H | H | F | H | H |
| 89 | Cl | H | H | H | Cl | H | H |
| 90 | Cl | H | H | H | H | H | H |
| 91 | Cl | H | H | H | OCH$_3$ | H | H |
| 92 | CH$_3$ | H | OCH$_3$ | H | H | H | H |
| 93 | CH$_3$ | H | H | H | Cl | H | H |

TABLE 4

Compounds

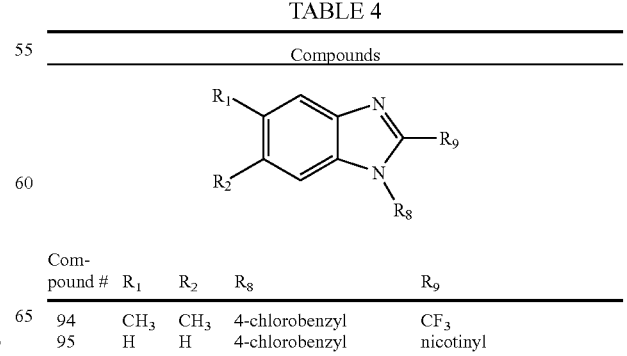

| Compound # | $R_1$ | $R_2$ | $R_8$ | $R_9$ |
|---|---|---|---|---|
| 94 | CH$_3$ | CH$_3$ | 4-chlorobenzyl | CF$_3$ |
| 95 | H | H | 4-chlorobenzyl | nicotinyl |

TABLE 4-continued

Compounds

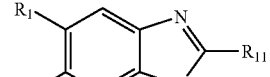

| Compound # | R₁ | R₂ | R₈ | R₉ |
|---|---|---|---|---|
| 96 | $CH_3$ | $CH_3$ | thiophene-2-carbonyl | $CF_3$ |
| 97 | $CH_3$ | $CH_3$ | furan-2-carbonyl | $CF_3$ |
| 98 | H | H | furan-2-carbonyl | 4-(diethylamino)phenyl |
| 99 | $CH_3$ | $CH_3$ | 4-chlorobenzoyl | $CF_3$ |
| 100 | H | H | 2-methoxybenzyl | 2-methoxyphenyl |
| 101 | H | H | thiophene-2-carbonyl | 4-(diethylamino)phenyl |

TABLE 6

Compounds

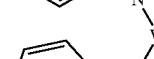

| Compound # | W | R₁ | R₂ | R₁₁ | R₁₂ |
|---|---|---|---|---|---|
| 129 | $CH_2$ | $CH_3$ | H | 2-furyl | 4-methyl-benzenesulfonyl |
| 130 | $CH_2$ | $CH_3$ | H | 2-thiophenyl | 4-methyl-benzenesulfonyl |

TABLE 5

Compounds

| Compound # | R₁ | R₂ | R₃ | R₄ | R₅ | R₆ | R₇ | R₁₀ |
|---|---|---|---|---|---|---|---|---|
| 102 | Cl | H | H | H | H | H | H | 4-methyl-benzenesulfonyl |
| 103 | H | H | H | H | H | H | H | 4-methyl-benzenesulfonyl |
| 104 | $CH_3$ | H | H | H | H | H | H | 4-methyl-benzenesulfonyl |
| 105 | $CH_3$ | $CH_3$ | H | H | H | H | H | 4-methyl-benzenesulfonyl |
| 106 | H | $CH_3$ | H | H | H | H | H | 4-methyl-benzenesulfonyl |
| 107 | H | H | $OCH_3$ | H | H | H | H | 4-methyl-benzenesulfonyl |
| 108 | $CH_3$ | H | $OCH_3$ | H | H | H | H | 4-methyl-benzenesulfonyl |
| 109 | H | H | $OC_2H_5$ | H | H | H | H | 4-methyl-benzenesulfonyl |
| 110 | H | H | H | $OCH_3$ | H | H | H | 4-methyl-benzenesulfonyl |
| 111 | H | H | Cl | H | H | H | H | 4-methyl-benzenesulfonyl |
| 112 | H | H | H | Cl | H | H | H | 4-methyl-benzenesulfonyl |
| 113 | H | H | H | H | Cl | H | H | 4-methyl-benzenesulfonyl |
| 114 | H | H | H | H | $OCH_3$ | H | H | 4-methyl-benzenesulfonyl |
| 115 | $CH_3$ | H | H | $OCH_3$ | H | H | H | 4-methyl-benzenesulfonyl |
| 116 | $CH_3$ | H | H | H | $OCH_3$ | H | H | 4-methyl-benzenesulfonyl |
| 117 | $CH_3$ | H | $OC_2H_5$ | H | H | H | H | 4-methyl-benzenesulfonyl |
| 118 | Cl | H | $OCH_3$ | H | H | H | H | 4-methyl-benzenesulfonyl |
| 119 | $CH_3$ | H | H | H | Cl | H | H | 4-methyl-benzenesulfonyl |
| 120 | $CH_3$ | H | H | Cl | H | H | H | 4-methyl-benzenesulfonyl |
| 121 | $CH_3$ | H | H | H | $CH_3$ | H | H | 4-methyl-benzenesulfonyl |
| 122 | $CH_3$ | H | $CH_3$ | H | H | H | H | 4-methyl-benzenesulfonyl |
| 123 | $CH_3$ | H | H | $CH_3$ | H | H | H | 4-methyl-benzenesulfonyl |
| 124 | $CH_3$ | H | Cl | H | H | H | H | 4-methyl-benzenesulfonyl |
| 125 | H | CN | H | H | H | H | H | 4-methyl-benzenesulfonyl |
| 126 | $CH_3$ | H | F | H | H | H | H | 4-methyl-benzenesulfonyl |
| 127 | $CH_3$ | H | H | H | H | H | H | phenylsulfonyl |
| 128 | $CH_3$ | H | H | H | H | H | H | methylsulfonyl |

TABLE 6-continued

Compounds

| Compound # | W | $R_1$ | $R_2$ | $R_{11}$ | $R_{12}$ |
|---|---|---|---|---|---|
| 131 | $CH_2$ | H | H | 2-furyl | 4-methyl-benzenesulfonyl |
| 132 | $SO_2$ | H | H | 4-diethylaminophenyl | 4-methyl-benzenesulfonyl |
| 133 | $CH_2$ | $CH_3$ | H | 3-pyridinyl | 4-methyl-benzenesulfonyl |
| 134 | $CH_2$ | $CH_3$ | H | 4-pyridinyl | 4-methyl-benzenesulfonyl |

The benzimidazole compounds described herein can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The route shown in Scheme 1 exemplifies synthesis of certain benzimidazole compounds of the present invention ($R^3$ and $R^5$ defined above). The 5-substituted 2-nitroaniline 1 reacts with an acyl chloride 2 to afford compound 3. The nitro group within compound 3 is reduced (iron powder, $NH_4Cl$, 100° C. or sodium hydrosulfite in ethanol, reflux) to provide the aniline 4. The Schiff base 5, formed by reacting compound 4 and 3,4,5-trimethoxybenaldehyde in methanol, is treated with sodium borohydride at room temperature to yield compound 6. The cyclization of compound 6 in the presence of 4N HCl in methanol then affords the final compound 7.

Scheme 1

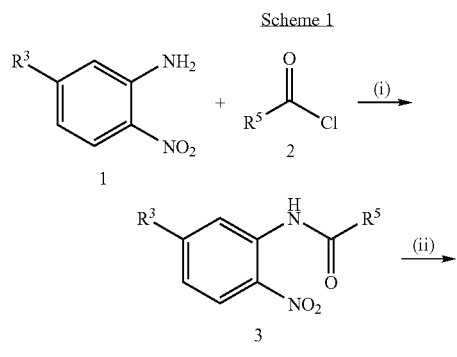

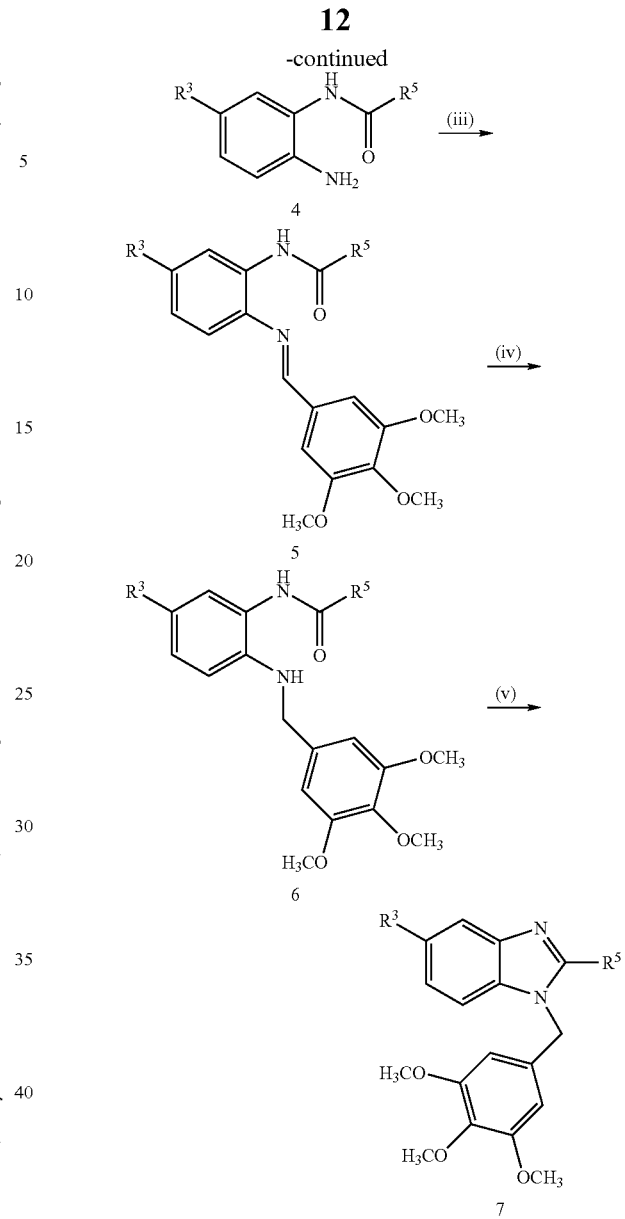

Reagents and conditions: (i) pyridine, $CH_2Cl_2$, rt; (ii) Fe, $NH_4Cl$, IPA, 100° C.; or $Na_2S_2O_4$, ethanol, reflux (iii) 3,4,5-trimethoxybenzaldehyde, MeOH, rt; (iv) $NaBH_4$, MeOH; (v) MeOH/4N HCl (2:1), 50° C.

A benzimidazole compound thus synthesized can be further purified by flash column chromatography, high performance liquid chromatography, crystallization, or any other suitable methods.

The benzimidazole compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the benzimidazole compounds of this invention and a pharmaceutically acceptable carrier, and (2) a method for treating cancer by administering to a subject in need of this treatment an effective amount of such a benzimidazole compound.

As used herein, the term "treating" refers to administering a benzimidazole compound to a subject that has cancer, or has a symptom of or a predisposition toward it, with the purpose to prevent, cure, heal, alleviate, relieve, alter, remedy, ameliorate, improve, or affect the disorder, the symptoms of or the predisposition toward the cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention includes both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A benzimidazole compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the active benzimidazole compounds can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the benzimidazole compounds in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 5-methyl-2-phenyl-1-(3,4,5-trimethoxybenzyl)-1H-benzo[d]imidazole (Compound 5)

N-(5-methyl-2-nitrophenyl)benzamide

To a stirred solution of 5-methyl-2-nitroaniline (4 mmol) and pyridine (8 mmol) in dry dichloromethane (15 mL) was added dropwise benzoyl chloride (8 mmol). The reaction mixture was stirred at room temperature for 8 h. The solvent was evaporated in vacuum, and the residue was subjected to flash chromatography on silica gel using a mixture of hexanes and $CH_2Cl_2$ (7:3) as eluent to afford N-(5-methyl-2-nitrophenyl)benzamide as a solid.

N-(2-amino-5-methylphenyl)benzamide

To a suspension of N-(5-methyl-2-nitrophenyl)benzamide (3 mmol) in isopropanol (150 mL) was added iron powder (2 g) and ammonium chloride (0.3 mmol). The reaction mixture was heated at 100° C. for 12 h. The hot mixture was filtered off and the filtrate was evaporated. The residue was subjected to flash chromatography on silica gel using a mixture of hexanes and $CH_2Cl_2$ (9:1) as eluent to afford N-(2-amino-5-methylphenyl)benzamide as a white-gray solid.

(E)-N-(5-methyl-2-(3,4,5-trimethoxybenzylideneamino)phenyl)benzamide

A mixture of N-(2-amino-5-methylphenyl)benzamide (2 mmol) and 3,4,5-trimethoxybenzaldehyde (3 mmol) in methanol was stirred at room temperature for 12 h. The suspension was filtered and the solid was washed with methanol to afford (E)-N-(5-methyl-2-(3,4,5-trimethoxybenzylideneamino)phenyl)benzamide as a yellow solid.

N-(5-methyl-2-(3,4,5-trimethoxybenzylamino)phenyl)benzamide

A suspension of compound (E)-N-(5-methyl-2-(3,4,5-trimethoxybenzylideneamino)phenyl)benzamide (3 mmol) in methanol was cooled with an ice bath. Sodium borohydride was added until the color turned white. Excess sodium borohydride was quenched by the addition of distilled water. The resulting mixture was extracted with ethyl acetate (50 mL×3). The combined organics were washed with brine, dried over anhydrous $MgSO_4$, and concentrated in vacuum to obtain N-(5-methyl-2-(3,4,5-trimethoxybenzylamino)phenyl)benzamide as a solid.

5-methyl-2-phenyl-1-(3,4,5-trimethoxybenzyl)-1H-benzo[d]imidazole

To a suspension of N-(5-methyl-2-(3,4,5-trimethoxybenzylamino)phenyl)benzamide in ethanol (20 mL) was added 4 N HCl. The reaction mixture was heated at 50° C. for 5 h, then cooled to room temperature. Excess acid was neutralized with ammonia hydroxide, and the resulting mixture was extracted with ethyl acetate (50 mL×3). The combined organics were washed with brine, dried over anhydrous $MgSO_4$, and concentrated in vacuum. The residue was subjected to flash chromatography on silica gel to obtain 5-methyl-2-phenyl-1-(3,4,5-trimethoxybenzyl)-1H-benzo[d]imidazole as a solid.

$^1$H NMR (400 MHz, DMSO-$d_6$) δ (ppm): 7.83-7.79 (m, 3H, 4, 2', 6'-H), 7.48-7.37 (m, 4H, 7, 3', 4', 5'-H), 7.07 (dd, J=8, 2 Hz, 1H, 6H), 6.29 (s, 2H, 2", 6"-H), 5.34 (s, 2H, $CH_2$), 3.57 (s, 9H, $OCH_3$), 2.40 (s, 3H, $CH_3$); $^{13}$C NMR (100 MHz, DMSO-$d_6$) δ (ppm): 164.6, 162.1, 153.5, 153.5, 152.8, 143.4, 137.1, 134.5, 133.0, 131.9, 131.9, 127.4, 124.6, 119.5, 116.3, 119.6, 111.2, 104.1, 104.1, 60.4, 56.2, 56.2, 48.0, 21.6; EIMS: m/z 388 ($M^+$).

Example 2

Synthesis of 2-(2-fluorophenyl)-5-methyl-1-(3,4,5-trimethoxybenzyl)benzimidazole (Compound 30)

Compound 30 was prepared in a manner similar to that described in Example 1.

$^1$H NMR (400 MHz, DMSO-$d_6$) δ (ppm): 7.68-7.62 (m, 2H, 4,6'-H), 7.52-7.37 (m, 4H, 7, 3', 4', 5'-H), 7.10 (dd, J=8, 2 Hz, 1H, 6-H), 6.25 (s, 2H, 2", 6"-H), 5.27 (s, 2H, $CH_2$), 3.57 (s, 3H, $OCH_3$), 3.55 (s, 6H, $OCH_3$), 2.41 (s, 3H, $CH_3$); $^{13}$C NMR (100 MHz, DMSO-$d_6$) δ (ppm): 161.3, 158.9, 153.3, 153.3, 148.6, 143.6, 137.3, 133.7, 132.9, 132.8, 131.8, 125.5, 124.5, 119.6, 116.8, 116.6, 111.3, 104.7, 104.7, 60.2, 56.5, 56.5, 47.9, 21.6; EIMS: m/z 406 ($M^+$).

Example 3

Synthesis of 2-(2-chlorophenyl)-5-methyl-1-(3,4,5-trimethoxybenzyl)benzimidazole (Compound 45)

Compound 45 was prepared in a manner similar to that described in Example 1.

$^1$H NMR (400 MHz, DMSO-$d_6$) δ (ppm): 7.67-7.60 (m, 2H, 4,7-H), 7.54-7.48 (m, 4H, 3', 4', 5', 6'-H), 7.10 (dd, J=8, 2 Hz, 1H, 6H), 6.26 (s, 2H, 2", 6"-H), 5.19 (s, 2H, $CH_2$), 3.58 (s, 3H, $OCH_3$), 3.54 (s, 3H, $OCH_3$), 2.41 (s, 3H, $CH_3$); $^{13}$C NMR (100 MHz, DMSO-$d_6$) δ (ppm): 153.3, 153.3, 150.7, 143.4, 137.2, 133.7, 133.3, 133.1, 132.4, 132.4, 132.3, 131.7, 130.3, 127.9, 124.7, 119.6, 111.3, 104.8, 104.8, 60.3, 56.2, 56.2, 47.9, 21.6; EIMS: m/z 422 ($M^+$).

Example 4

Synthesis of 2-(2-ethoxyphenyl)-5-methyl-1-(3,4,5-trimethoxybenzyl)benzimidazole (Compound 48)

Compound 48 was prepared in a manner similar to that described in Example 1.

$^1$H NMR (400 MHz, DMSO-$d_6$) δ (ppm): 7.52-7.44 (m, 5H, 4, 7, 3', 4, 5', 6'-H), 7.20 (d, J=8 Hz, 1H, 4'H), 7.10 (t, J=7 Hz, 1H, 5'-H), 7.05 (d, J=8 Hz, 1H, 3'H), 6.25 (s, 2H, 2", 6"-H), 5.19 (s, 2H, $CH_2$), 4.10 (q, J=7 Hz, 3H, $OCH_2$) 3.59 (s, 6H, $OCH_3$), 3.56 (s, 3H, $OCH_3$), 2.40 (s, 3H, $CH_3$), 1.20 (t, J=7 Hz, 3H, $OCH_2CH_3$); $^{13}$C NMR (100 MHz, DMSO-$d_6$) δ (ppm): 156.6, 153.2, 153.2, 151.9, 143.8, 137.2, 133.6, 132.9, 132.9, 132.1, 131.1, 124.1, 121.1, 120.4, 119.3, 113.1, 111.0, 105.0, 105.0, 64.1, 60.4, 56.2, 56.2, 48.0, 21.6, 14.9; EIMS: m/z 432 ($M^+$).

Example 5

Synthesis of 2-(2-hydroxyphenyl)-5-methyl-1-(3,4,5-trimethoxybenzyl)benzimidazole (Compound 53)

Compound 53 was prepared in a manner similar to that described in Example 1.

$^1$H-NMR (200 MHz, CDCl$_3$-$d_1$) δ (ppm): 7.62 (s, 1H, 4-H), 7.41 (d, J=8 Hz, 1H, 6-H), 7.28-7.13 (m, 4H, 7, 3', 4', 6'-H), 6.82 (t, J=6 Hz, 1H, 5'-H), 6.34 (s, 2H, 2", 6"-H), 5.45 (s, 2H. $CH_2$) 3.81 (s, 3H, $OCH_3$), 3.7 (s, 6H, $OCH_3$), 2.5 (s, 3H, $CH_3$); $^{13}$C-NMR (50 MHz, CDCl$_3$-$d_1$) δ (ppm): 159.1, 154.6, 154.6, 152.3, 140.5, 138.2, 134.3, 134.0, 132.6, 131.9, 127.9, 126.1, 119.6, 119.0, 118.6, 113.0, 110.5, 103.6, 103.6, 61.5, 56.8, 56.8, 50.1, 22.2; EIMS: m/z 404 ($M^+$).

Example 6

Synthesis of 5-methyl-2-(pyridin-4-yl)-1-(3,4,5-trimethoxybenzyl)benzimidazole (Compound 70)

Compound 70 was prepared in a manner similar to that described in Example 1.

$^1$H NMR (400 MHz, DMSO-$d_6$) δ (ppm): 8.74 (d, J=6 Hz, 1H, 2',6'-H), 7.76 (d, J=6 Hz, 1H, 3',5'-H), 7.54-7.51 (m, 2H, 4,7-H), 7.13 (d, J=8 Hz, 1H, 6-H), 6.28 (s, 2H, 2", 6"-H), 5.52 (s, 2H, $CH_2$) 3.57 (s, 9H, $OCH_3$), 2.42 (s, 3H, $CH_3$); $^{13}$C NMR (100 MHz, DMSO-d$_6$) δ (ppm): 153.0, 153.0, 150.5, 150.2, 150.2, 142.8, 137.7, 136.7, 134.3, 132.3, 131.7, 124.9, 123.2, 123.2, 119.3, 110.9, 103.7, 103.7, 59.9, 55.7, 55.7, 47.6, 21.1; EIMS: m/z 389.0 (M$^+$).

Example 7

Synthesis of 5-methyl-2-propyl-1-(3,4,5-trimethoxybenzyl)benzimidazole (Compound 71)

Compound 71 was prepared in a manner similar to that described in Example 1.

$^1$H NMR (400 MHz, DMSO-d$_6$) δ (ppm): 7.35 (d, J=2 Hz, 1H, 4-H), 7.31 (d, J=8 Hz, 1H, 7-H), 6.96 (dd, J=8, 2 Hz, 1H, 6-H), 6.40 (s, 2H, 2", 6"-H), 5.33 (s, 2H, CH$_2$), 3.63 (s, 6H, OCH$_3$), 3.60 (s, 3H, OCH$_3$), 2.81 (t, J=7 Hz, 2H, CH$_2$), 2.36 (s, 3H, CH$_3$), 1.78-1.72 (m, 2H, CH$_2$), 0.94 (t, J=7 Hz, 3H, CH$_3$); $^{13}$C NMR (100 MHz, DMSO-d$_6$) δ (ppm): 154.8, 153.0, 153.0, 142.7, 136.7, 133.3, 132.8, 130.1, 122.9, 122.9, 118.3, 118.3, 115.3, 111.4, 109.6, 109.6, 105.3, 103.9, 103.9, 59.9, 55.8, 55.8, 46.1, 28.4, 21.1, 20.4, 13.7; EIMS: m/z 354.0 (M$^+$).

Example 8

Synthesis of 2-(1-adamantyl)-5-methyl-1-(3,4,5-trimethoxybenzyl)benzimidazole (Compound 72)

Compound 72 was prepared in a manner similar to that described in Example 1.

$^1$H NMR (400 MHz, DMSO-d$_6$) δ (ppm): 7.36 (s, 1H, 4-H), 6.99 (d, J=8 Hz, 1H, 6-H), 6.90 (d, J=8 Hz, 1H, 7-H), 6.25 (s, 2H, 2", 6"-H), 5.61 (s, 2H, CH$_2$), 3.58 (s, 9H, OCH$_3$), 2.35 (s, 3H, CH$_3$), 2.13 (br s, 6H, CH$_2$), 2.02 (br s, 3H, CH), 1.79-1.69 (m, 6H, CH$_2$); $^{13}$C NMR (100 MHz, DMSO-d$_6$) δ (ppm): 171.0, 171.0, 154.7, 139.2, 139.2, 126.1, 126.1, 125.5, 125.5, 124.7, 124.7, 123.6, 122.3, 116.0, 116.0, 35.4, 35.4, 29.6, 28.1, 27.4, 27.4, 21.8, 21.8, 21.8, 21.2, 21.2, 13.7, 13.7; EIMS: m/z 446.0 (M$^+$).

Example 9

Synthesis of 5-methyl-2-(1'-naphthyl)-1-(3,4,5-trimethoxybenzyl)benzimidazole (Compound 73)

Compound 73 was prepared in a manner similar to that described in Example 1.

$^1$H NMR (400 MHz, DMSO-d$_6$) δ (ppm): 8.13 (d, J=8 Hz, 1H, 8'-H), 8.04 (d, J=8 Hz, 1H, 2'-H), 7.76 (t, J=8 Hz, 2H, 7',6'-H), 7.67 (t, J=8 Hz, 1H, 3'-H), 7.58-7.50 (m, 4H, 4, 7, 4', 5'-H), 7.12 (d, J=8 Hz, 1H, 6-H), 6.10 (s, 2H, 2", 6"-H), 5.22 (s, 2H, CH$_2$), 3.47 (s, 3H, OCH$_3$), 3.41 (s, 6H, OCH$_3$), 2.44 (s, 3H, CH$_3$); $^{13}$C NMR (100 MHz, DMSO-d$_6$) δ (ppm): 153.2, 153.2, 152.1, 143.6, 137.1, 133.7, 132.5, 132.2, 131.7, 130.6, 129.2, 128.9, 128.2, 127.6, 127.0, 125.8, 125.7, 124.6, 119.6, 111.3, 104.8, 104.8, 60.3, 56.0, 56.0, 47.9, 21.7; EIMS: m/z 438 (M$^+$).

Example 10

Synthesis of 5-methyl-2-(2'-naphthyl)-1-(3,4,5-trimethoxybenzyl)benzimidazole (Compound 74)

Compound 74 was prepared in a manner similar to that described in Example 1.

$^1$H NMR (400 MHz, DMSO-d$_6$) δ (ppm): 8.33 (d, J=2 Hz, 1H, 1'-H), 8.07 (d, J=8 Hz, 1H, 4-H), 8.00-7.79 (m, 2H, 5,8-H), 7.89 (dd, J=8, 2 Hz, 1H, 3'-H), 7.61-7.52 (m, 4H, 4, 7, 6', 7'-H), 7.11 (d, J=8 Hz, 1H, 6-H) 6.30 (s, 2H, 2", 6"-H), 5.54 (s, 2H, CH$_2$), 3.55 (s, 6H, OCH$_3$), 3.50 (s, 3H, OCH$_3$), 2.43 (s, 3H, CH$_3$); $^{13}$C NMR (100 MHz, DMSO-d$_6$) δ (ppm): 153.1, 152.9, 152.9, 143.1, 136.7, 134.2, 133.0, 132.6, 132.5, 131.3, 128.8, 128.3, 128.3, 127.9, 127.6, 127.3, 126.8, 126.3, 124.2, 118.9, 110.7, 103.9, 103.9, 59.9, 55.6, 55.6, 47.6, 21.2; EIMS: m/z 455 (M$^+$).

Example 11

Synthesis of 2-phenyl-5-(pyrrolidin-1-yl)-1-(3,4,5-trimethoxybenzyl)-1H-benzo[d]imidazole (Compound 55)

2-Nitro-5-(pyrrolidin-1-yl)benzenamine

A mixture of 5-chloro-2-nitroaniline (1.73 g, 10 mmol) and pyrrolidine (1.42 g, 20 mmole) was refluxed in a pressure vessel for 6 h. Solvent was evaporated and the residue was diluted with ethyl acetate. The resulting mixture was washed with aqueous NaHCO$_3$ (5%) and distilled water, dried over MgSO$_4$, and concentrated to afford 2-nitro-5-(pyrrolidin-1-yl)benzenamine as a solid (93% yield). $^1$H NMR (400 MHz, CDCl$_3$) δ (ppm): 7.80 (d, J=8 Hz, 1H, 3-H), 7.22 (s, 2H, NH$_2$), 6.05 (dd, J=8, 2 Hz, 1H, 4-H), 5.81 (d, J=2 Hz, 1H, 6-H), 3.30-3.27 (m, 4H, 2',5'-H), 1.97-1.91 (m, 4H, 3',4'-H). $^{13}$C NMR (100 MHz, CDCl$_3$-d$_1$) δ (ppm): 151.9, 148.3, 127.4, 122.1, 104.7, 94.5, 47.3, 47.3, 24.8, 24.8; EIMS: m/z 207 (M$^+$).

N-(2-nitro-5-(pyrrolidin-1-yl)phenyl)benzamide

To a stirred solution of 2-nitro-5-(pyrrolidin-1-yl)benzenamine (4 mmol) and pyridine (8 mmol) in dry dichloromethane (15 mL) was added dropwise benzoyl chloride (8 mmol). The reaction mixture was stirred at room temperature for 8 h. The solvent was evaporated in vacuum, and the residue was subjected to flash chromatography on silica gel using a mixture of hexanes and CH$_2$Cl$_2$ as eluent to afford N-(2-nitro-5-(pyrrolidin-1-yl)phenyl)benzamide as a solid.

N-(2-amino-5-(pyrrolidin-1-yl)phenyl)benzamide

A mixture of N-(2-nitro-5-(pyrrolidin-1-yl)phenyl)benzamide and sodium hydrosulfite (9 mmol) (3 mmol) in ethanol (150 mL) was refluxed for 1 h. After cooled to room temperature, the mixture was extracted with ethyl acetate (50 mL×3). The combined organics were washed with brine, dried over anhydrous MgSO$_4$, and concentrated in vacuum to give crude N-(2-amino-5-(pyrrolidin-1-yl)phenyl)benzamide.

(E)-N-(5-(pyrrolidin-1-yl)-2-(3,4,5-trimethoxybenzylideneamino)phenyl)benzamide

A mixture of N-(2-amino-5-(pyrrolidin-1-yl)phenyl)benzamide (2 mmol) and 3,4,5-trimethoxybenzaldehyde (3 mmol) in methanol was stirred at room temperature for 12 h. The suspension was filtered and the solid was washed with methanol to afford (E)-N-(5-(pyrrolidin-1-yl)-2-(3,4,5-trimethoxybenzylideneamino)phenyl)benzamide as a yellow solid.

N-(5-(pyrrolidin-1-yl)-2-(3,4,5-trimethoxybenzylamino)phenyl)benzamide

A suspension of compound (E)-N-(5-(pyrrolidin-1-yl)-2-(3,4,5-trimethoxybenzylideneamino)phenyl)benzamide (3 mmol) in methanol was cooled with an ice bath. Sodium borohydride was added until the color turned white. Excess sodium borohydride was quenched by the addition of distilled water. The resulting mixture was extracted with ethyl acetate (50 mL×3). The combined organics were washed with brine, dried over anhydrous MgSO$_4$, and concentrated in vacuum to obtain N-(5-(pyrrolidin-1-yl)-2-(3,4,5-trimethoxybenzylamino)phenyl)benzamide as a solid.

2-phenyl-5-(pyrrolidin-1-yl)-1-(3,4,5-trimethoxybenzyl)-1H-benzo[d]imidazole

To a suspension of N-(5-(pyrrolidin-1-yl)-2-(3,4,5-trimethoxybenzylamino)phenyl)benzamide in ethanol (20 mL) was added 4 N HCl. The reaction mixture was heated at 50° C. for 5 h, then cooled to room temperature. Excess acid was neutralized with ammonia hydroxide, and the resulting mixture was extracted with ethyl acetate (50 mL×3). The combined organics were washed with brine, dried over anhydrous MgSO$_4$, and concentrated in vacuum. The residue was subjected to flash chromatography on silica gel to obtain 2-phenyl-5-(pyrrolidin-1-yl)-1-(3,4,5-trimethoxybenzyl)-1H-benzo[d]imidazole as a solid. $^1$H NMR (400 MHz, DMSO-d$_6$) δ (ppm): 7.75-7.72 (m, 2H, 2',6'-H), 7.55-7.50 (m, 3H, 3', 4', 5'-H), 7.34 (d, J=8 Hz, 1H, 7-H), 7.75 (d, J=2 Hz, 1H, 4-H), 6.60 (dd, J=8, 2 Hz, 1H, 6-H), 6.29 (s, 2H, 2", 6"-H), 5.38 (s, 2H, CH$_2$), 3.56 (s, 9H, OCH$_3$), 3.25-3.22 (m, 4H, 2',5'-H), 1.97-1.94 (m, 4H, 3',4'-H); $^{13}$C NMR (100 MHz, DMSO-d$_6$) δ (ppm): 152.9, 152.9, 152.5, 144.8, 144.0, 136.6, 132.7, 130.7, 129.4, 128.9, 128.9, 128.7, 128.7, 127.9, 111.1, 109.9, 103.7, 103.7, 99.9, 59.8, 55.7, 55.7, 47.9, 47.9, 47.7, 24.8, 24.8; EIMS: m/z 443 (M$^+$).

Example 12

Synthesis of 2-(2-ethoxyphenyl)-5-(pyrrolidin-1-yl)-1-(3,4,5-trimethoxybenzyl)benzimidazole (Compound 64)

Compound 64 was prepared in a manner similar to that described in Example 11.
$^1$H-NMR (200 MH$_Z$, CDCl$_3$-d$_1$) δ (ppm): 7.58-7.44 (m, 2H, 4,7-H), 7.13-7.08 (m, 4H, 3', 4', 5', 6'-H), 6.64 (d, J=9 Hz, 1H, 6-H), 6.18 (s, 2H, 2", 6"-H), 5.16 (s, 2H, CH$_2$), 4.08-3.85 (m, 2H, OCH$_2$), 3.76 (s, 3H, OCH$_3$), 3.69 (s, 6H, OCH$_3$), 3.34-3.28 (m, 4H, CH$_2$), 2.04-1.97 (m, 4H, CH$_2$), 1.27-1.18 (m, 3H, OCH$_2$OCH$_3$); $^{13}$C-NMR (50 MH$_Z$, CDCl$_3$-d$_1$) δ (ppm): 156.5, 153.2, 153.2, 150.5, 145.3, 142.9, 137.2, 132.5, 131.7, 126.6, 120.8, 119.0, 112.3, 110.8, 110.1, 103.9, 103.9, 99.8, 64.5, 64.1, 60.7, 55.9, 55.9, 48.5, 48.3, 48.3, 25.3, 25.3, 14.1; EIMS: m/z 487 (M$^+$).

Example 13

Synthesis of 2-(furan-2-yl)-5-(pyrrolidin-1-yl)-1-(3,4,5-trimethoxybenzyl)benzimidazole (Compound 77)

Compound 77 was prepared in a manner similar to that described in Example 11.
$^1$H-NMR (400 MH$_Z$, CDCl$_3$-d$_1$) δ (ppm): 7.56 (s, 1H, 4-H), 7.50 (d, J=9 Hz, 1H, 3'-H), 7.14 (s, J=9 Hz, 1H, 7-H), 6.90 (s, 1H, 5'-H), 6.6 (dd, J=9, 2 Hz, 1H, 6-H), 6.56-6.55 (m, 1H, 4'-H), 6.40 (s, 2H, 2", 6"-H), 5.57 (s, 2H, CH$_2$), 3.78 (s, 3H, OCH$_3$), 3.69 (s, 6H, OCH$_3$), 3.30-3.27 (m, 5H, CH$_2$), 1.99-1.97 (m, 3H, CH$_2$); $^{13}$C-NMR (100 MH$_Z$, CDCl$_3$-d$_1$) δ (ppm): 159.1, 154.6, 154.6, 152.3, 140.5, 138.2, 134.3, 134.0, 132.6, 131.9, 127.9, 126.1, 119.6, 119.0, 118.6, 113.0, 110.5, 103.6, 103.6, 61.5, 56.8, 56.8, 50.1, 22.2; EIMS: m/z 433 (M$^+$).

Example 14

Synthesis of 5-(pyrrolidin-1-yl)-1-(3,4,5-trimethoxybenzyl)-2-(thiophen-2-yl)benzimidazole (Compound 78)

Compound 78 was prepared in a manner similar to that described in Example 11.
$^1$H-NMR (200 MH$_Z$, CDCl$_3$-d$_1$) δ (ppm): 7.87-7.83 (m, 1H, 3'-H), 7.47-7.42 (m, 2H, 4',5'-H), 7.07 (s, 1H, 7-H), 7.06-7.03 (m, 1H, 4-H), 6.63 (dd, J=9, 2, 1H, 6-H), 6.31 (s, 2H, 2", 6"-H), 5.43 (s, 2H, CH$_2$), 3.80 (s, 3H$_2$OCH$_3$), 3.69 (s, 6H, OCH$_3$), 3.29-3.09 (m, 5H, CH$_2$), 2.02-1.98 (m, 3H, CH$_2$); $^{13}$C-NMR (50 MH$_Z$, CDCl$_3$-d$_1$) δ (ppm): 153.8, 147.4, 145.6, 144.3, 137.3, 132.4, 132.1, 128.4, 127.8, 127.2, 116.9, 110.5, 110.1, 102.7, 100.4, 93.8, 60.8, 56.1, 56.1, 48.3, 48.3, 29.7, 25.4, 25.4, 14.2; EIMS: m/z 449 (M$^+$).

Example 15

Synthesis of 5,6-dimethyl-2-phenyl-1-((1-tosyl-indol-3-yl)methyl)benzimidazole (Compound 105)

Compound 105 was prepared in a manner similar to that described in Example 1.
$^1$H-NMR (200 MH$_Z$, CDCl$_3$-d$_1$) δ (ppm): 8.00 (d, J=8 Hz, 1H, ArH), 7.70-7.58 (m, 5H, ArH), 7.47-7.34 (m, 5H, ArH), 7.24-7.13 (m, 4H, ArH), 7.00 (s, 1H, ArH), 5.48 (s, 2H, CH$_2$), 2.38 (s, 3H, CH$_3$), 2.32 (s, 3H, CH$_3$), 2.31 (s, 3H, CH$_3$); $^{13}$C-NMR (50 MH$_Z$, CDCl$_3$-d$_1$) δ (ppm): 151.6, 145.1, 138.4, 135.5, 134.7, 133.5, 133.4, 133.2, 130.6, 129.9, 129.9, 129.1, 129.1, 129.0, 129.0, 128.3, 127.8, 126.7, 126.7, 125.5, 123.9, 123.7, 118.9, 118.9, 117.9, 114.1, 110.6, 41.6, 21.5, 20.6, 20.2; ESI: m/z 506 (M+1)$^+$.

Example 16

Synthesis of 6-methyl-2-phenyl-1-((1-tosyl-indol-3-yl)methyl)benzimidazole (Compound 106)

Compound 106 was prepared in a manner similar to that described in Example 1.
$^1$H-NMR (200 MH$_Z$, CDCl$_3$-d$_1$) δ (ppm): 8.01 (d, J=8 Hz, 1H, ArH), 7.76 (d, J=8 Hz, 1H, ArH), 7.66 (dd, J=8, 1 Hz, 2H, ArH), 7.59 (d, J=8 Hz, 2H, ArH), 7.48-7.21 (m, 6H, ArH), 7.16-7.13 (m, 4H, ArH), 6.98 (s, 1H, ArH), 5.44 (s, 2H, CH$_2$), 2.41 (s, 3H, CH$_3$), 2.32 (s, 3H, CH$_3$); $^{13}$C-NMR (50 MH$_Z$, CDCl$_3$-d$_1$) δ (ppm): 152.9, 145.1, 140.6, 135.9, 134.8, 133.4, 130.0, 129.8, 129.5, 129.5, 129.0, 129.0, 128.8, 128.8, 128.4, 126.7, 126.7, 125.5, 125.5, 124.7, 123.9, 123.6, 119.5, 119.0, 118.6, 114.1, 110.0, 41.3, 21.8, 21.5; ESI: m/z 492 (M+1)$^+$.

Example 17

Synthesis of 2-(2-methoxyphenyl)-1-((1-tosyl-indol-3-yl)methyl)benzimidazole (Compound 107)

Compound 107 was prepared in a manner similar to that described in Example 1.
$^1$H-NMR (200 MH$_Z$, CDCl$_3$-d$_1$) δ (ppm): 7.93 (d, J=8 Hz, 1H, ArH), 7.85 (d, J=8 Hz, 1H, ArH), 7.59-7.47 (m, 4H, ArH), 7.31-7.24 (m, 2H, ArH), 7.16-7.09 (m, 7H, ArH), 7.04-6.95 (m, 2H, ArH), 5.30 (s, 2H, CH$_2$), 3.61 (s, 3H, OCH$_3$), 2.32 (s, 3H, CH₃); ¹³C-NMR (50 MH$_z$, CDCl₃-d₁) δ (ppm): 157.5, 151.6, 145.0, 142.8, 135.1, 134.8, 134.8, 132.3, 132.3, 131.9, 129.8, 129.8, 128.9, 126.7, 126.7, 125.1, 124.5, 123.4, 122.7, 122.4, 121.0, 119.9, 119.0, 117.8, 113.8, 111.1, 110.4, 55.4, 40.6, 21.5; ESI: m/z 508 (M+1)⁺.

Example 18

Synthesis of 2-(2-methoxyphenyl)-5-methyl-1-((1-tosylindol-3-yl)methyl)benzoimidazole (Compound 108)

Compound 108 was prepared in a manner similar to that described in Example 1.
¹H-NMR (200 MH$_z$, CDCl₃-d₁) δ (ppm): 7.92 (d, J=8 Hz, 1H, ArH), 7.60-7.51 (m, 3H, ArH), 7.46-7.38 (m, 2H, ArH), 7.33-7.20 (m, 2H, ArH), 7.15-7.06 (m, 4H, ArH), 7.03-6.90 (m, 4H, ArH), 5.24 (s, 2H, CH₂), 3.56 (s, 3H, O CH₃), 2.45 (s, 3H, CH₃), 2.29 (s, 3H, CH₃); ¹³C-NMR (50 MH$_z$, CDCl₃-d₁) δ (ppm): 157.3, 156.8, 151.6, 144.9, 143.4, 135.0, 134.7, 133.0, 132.0, 131.6, 129.7, 129.7, 128.9, 126.5, 126.5, 124.9, 124.3, 123.9, 123.3, 120.8, 119.6, 119.2, 119.0, 118.0, 113.7, 110.9, 109.7, 55.2, 40.4, 21.4, 21.4; ESI: m/z 522 (M+1)⁺.

Example 19

Synthesis of 2-(2-ethoxyphenyl)-1-((1-tosyl-indol-3-yl)methyl)benzimidazole (Compound 109)

Compound 109 was prepared in a manner similar to that described in Example 1.
¹H-NMR (200 MH$_z$, CDCl₃-d₁) δ (ppm): 7.92-7.82 (m, 2H, ArH), 7.59-7.53 (m, 3H, ArH), 7.50-7.41 (m, 2H, ArH), 7.29-7.21 (m, 2H, ArH), 7.16-7.06 (m, 7H, ArH), 7.03-6.96 (m, 1H, ArH), 5.34 (d, J=1 Hz, 2H, CH₂), 3.99 (q, J=7 Hz, 2H, OCH₂CH₃), 2.32 (s, 3H, CH₃), 1.18 (t, J=7 Hz, 3H, OCH₂CH₃); ¹³C-NMR (50 MH$_z$, CDCl₃-d₁) δ (ppm): 156.8, 151.5, 145.0, 141.7, 135.1, 134.8, 134.4, 132.4, 132.2, 129.8, 129.8, 128.8, 126.7, 126.7, 125.1, 124.6, 123.4, 122.9, 122.7, 121.0, 119.6, 118.9, 118.5, 117.4, 113.8, 112.2, 110.5, 64.2, 40.7, 21.5, 14.5; ESI: m/z 522 (M+1)⁺.

Example 20

Synthesis of 2-(3-methoxyphenyl)-1-((1-tosyl-indol-3-yl)methyl)benzimidazole (Compound 110)

Compound 110 was prepared in a manner similar to that described in Example 1.
¹H-NMR (200 MH$_z$, CDCl₃-d₁) δ (ppm): 7.99 (d, J=8 Hz, 1H, ArH), 7.88 (d, J=8 Hz, 1H, ArH), 7.56 (d, J=8 Hz, 2H, ArH), 7.37-7.28 (m, 3H, ArH), 7.26-7.18 (m, 6H, ArH), 7.14-7.18 (m, 3H, ArH), 7.02-6.96 (m, 1H, ArH), 5.50 (d, J=1 Hz, 2H, CH₂), 2.32 (s, 3H, CH₃); ¹³C-NMR (50 MH$_z$, CDCl₃-d₁) δ (ppm): 159.8, 153.4, 145.1, 142.6, 135.6, 135.4, 134.6, 130.7, 129.8, 129.8, 129.8, 128.4, 126.7, 126.7, 125.4, 124.0, 123.6, 123.2, 122.9, 121.1, 120.0, 119.0, 118.5, 116.7, 114.1, 113.9, 110.2, 55.1, 41.2, 21.5; ESI: m/z 508 (M+1)⁺.

Example 21

Synthesis of 2-(2-chlorophenyl)-1-((1-tosyl-indol-3-yl)methyl)benzimidazole (Compound 111)

Compound III was prepared in a manner similar to that described in Example 1.
¹H-NMR (200 MH$_z$, CDCl₃-d₁) δ (ppm): 7.93-7.84 (m, 2H, ArH), 7.58 (d, J=8 Hz, 2H, ArH), 7.45-7.36 (m, 4H, ArH), 7.32-7.22 (m, 4H, ArH), 7.17-7.06 (m, 5H, ArH), 5.33 (s, 2H, CH₂), 2.31 (s, 3H, CH₃); ¹³C-NMR (50 MH$_z$, CDCl₃-d₁) δ (ppm): 150.9, 145.0, 142.6, 135.1, 134.7, 134.1, 134.1, 132.0, 131.5, 129.8, 129.8, 129.8, 129.5, 128.6, 126.9, 126.6, 126.6, 125.1, 124.3, 123.4, 123.2, 122.7, 120.2, 118.8, 117.3, 113.8, 110.4, 40.3, 21.5; ESI: m/z 512 M⁺.

Example 22

Synthesis of 2-(3-chlorophenyl)-1-((1-tosyl-indol-3-yl)methyl)benzimidazole (Compound 112)

Compound 112 was prepared in a manner similar to that described in Example 1.
¹H-NMR (200 MH$_z$, CDCl₃-d₁) δ (ppm): 8.00 (d, J=8 Hz, 1H, ArH), 7.88 (d, J=8 Hz, 1H, ArH), 7.73-7.71 (m, 1H, ArH), 7.59-7.49 (m, 3H, ArH), 7.45-7.24 (m, 6H, ArH), 7.21 (d, J=1 Hz, 2H, ArH), 7.17 (s, 1H, ArH), 7.13 (d, J=1 Hz, 2H, ArH), 5.48 (d, J=1 Hz, 2H, CH₂), 2.32 (s, 3H, CH₃); ¹³C-NMR (50 MH$_z$, CDCl₃-d₁) δ (ppm): 151.6, 145.2, 141.6, 135.5, 135.4, 135.1, 134.6, 130.5, 130.2, 129.9, 129.9, 129.3, 128.3, 127.1, 126.7, 126.7, 125.6, 124.9, 124.0, 123.9, 123.7, 123.6, 119.9, 118.9, 117.9, 114.2, 110.5, 41.4, 21.6; ESI: m/z 512 M⁺.

Example 23

Synthesis of 2-(4-chlorophenyl)-1-((1-tosyl-indol-3-yl)methyl)benzimidazole (Compound 113)

Compound 113 was prepared in a manner similar to that described in Example 1.
¹H-NMR (200 MH$_z$, CDCl₃-d₁) δ (ppm): 8.01 (d, J=8 Hz, 1H, ArH), 7.88 (d, J=8 Hz, 1H, ArH), 7.63-7.55 (m, 4H, ArH), 7.44-7.28 (m. 5H, ArH), 7.26-7.12 (m, 6H, ArH), 5.46 (s, 2H, CH₂), 2.34 (s, 3H, CH₃); ¹³C-NMR (50 MH$_z$, CDCl₃-d₁) δ (ppm): 152.2, 145.2, 142.2, 136.6, 135.6, 134.7, 130.3, 129.9, 129.9, 129.2, 129.2, 128.3, 128.3, 127.7, 126.7, 126.7, 125.6, 124.0, 123.7, 123.7, 123.4, 119.9, 118.9, 118.9, 118.2, 114.2, 110.3, 41.4, 21.5; ESI: m/z 512 M⁺.

Example 24

Synthesis of 2-(4-methoxyphenyl)-1-((1-tosyl-indol-3-yl)methyl)benzimidazole (Compound 114)

Compound 114 was prepared in a manner similar to that described in Example 1.
¹H-NMR (200 MH$_z$, CDCl₃-d₁) δ (ppm): 8.00 (d, J=8 Hz, 1H, ArH), 7.90 (d, J=8 Hz, 1H, ArH), 7.68-7.56 (m, 4H, ArH), 7.37-7.26 (m, 4H, ArH), 7.24-7.13 (m, 5H, ArH), 6.93 (d, J=2 Hz, 1H, ArH), 6.90 (d, J=2 Hz, 1H, ArH), 5.49 (d, J=1 Hz, 2H, CH₂), 3.82 (s, 3H, OCH₃), 2.33 (s, 3H, CH₃); ¹³C-NMR (50 MH$_z$, CDCl₃-d₁) δ (ppm): 161.5, 153.1, 145.1, 141.0, 135.6, 135.1, 134.7, 130.8, 130.8, 130.3, 129.9, 129.9, 128.4, 126.8, 126.8, 125.6, 124.1, 123.7, 123.5, 120.5, 119.3, 118.9, 118.1, 114.5, 114.5, 114.2, 110.3, 55.4, 41.6, 21.6; ESI: m/z 508 (M+1)⁺.

Example 25

Synthesis of 2-(3-methoxyphenyl)-5-methyl-1-((1-tosyl-indol-3-yl)methyl) Benzimidazole (Compound 115)

Compound 115 was prepared in a manner similar to that described in Example 1.

¹H-NMR (200 MH_Z, CDCl_3-d_1) δ (ppm): 7.99 (d, J=8 Hz, 1H, ArH), 7.68 (s, 1H, ArH), 7.59 (d, J=8 Hz, 2H, ArH), 7.37-7.08 (m, 9H, ArH), 7.08-6.97 (m, 3H, ArH), 5.49 (s, 2H, CH_2), 3.60 (s, 3H, OCH_3), 2.50 (s, 3H, CH_3), 2.33 (s, 3H, CH_3); ¹³C-NMR (100 MH_Z, CDCl_3-d_1) δ (ppm): 159.8, 153.3, 145.1, 142.8, 135.5, 134.7, 133.7, 132.8, 130.8, 129.8, 129.8, 129.8 128.5, 126.7, 126.7, 125.4, 124.8, 124.1, 123.6, 121.1, 119.7, 119.0, 118.6, 116.6, 114.1, 114.0, 109.9, 55.1, 41.3, 21.5, 21.5; ESI: m/z 522 (M+1)⁺.

Example 26

Synthesis of 2-(4-methoxyphenyl)-5-methyl-1-((1-tosyl-indol-3-yl)methyl)benzimidazole (Compound 116)

Compound 116 was prepared in a manner similar to that described in Example 1.
¹H-NMR (200 MH_Z, CDCl_3-d_1) δ (ppm): 7.99 (d, J=8 Hz, 1H, ArH), 7.67-7.57 (m, 6H, ArH), 7.38-7.31 (m, 1H, ArH), 7.19-7.13 (m, 4H, ArH), 7.05 (s, 2H, ArH), 6.89 (d, J=8 Hz, 2H, ArH), 5.47 (s, 2H, CH_2), 2.48 (s, 3H, CH_3), 2.33 (s, 3H, CH_3); ESI: m/z 522 (M+1)⁺.

Example 27

Synthesis of 2-(2-ethoxyphenyl)-5-methyl-1-((1-tosyl-indol-3-yl)methyl)benzimidazole (Compound 117)

Compound 117 was prepared in a manner similar to that described in Example 1.
¹H-NMR (200 MH_Z, CDCl_3-d_1) δ (ppm): 7.90 (d, J=8 Hz, 1H, ArH), 7.6 (s, 1H, ArH), 7.60-7.49 (m, 3H, ArH), 7.45-7.41 (m, 2H, ArH), 7.22-7.13 (m, 3H, ArH), 7.09-6.96 (m, 6H, ArH), 5.32 (s, 2H, CH_2), 3.99 (q, J=7 Hz, 2H, OCH_2CH_3), 2.47 (s, 3H, CH_3), 2.33 (s, 3H, CH_3), 1.18 (t, J=7 Hz, 3H, OCH_2CH_3); ESI: m/z 536 (M+1)⁺.

Example 28

Synthesis of 5-chloro-2-(2-methoxyphenyl)-1-((1-tosyl-indol-3-yl)methyl)benzimidazole (Compound 118)

Compound 118 was prepared in a manner similar to that described in Example 1.
¹H-NMR (200 MH_Z, CDCl_3-d_1) δ (ppm): 7.95 (d, J=8 Hz, 1H, ArH), 7.85 (d, J=2 Hz, 1H, ArH), 7.59-7.46 (m, 4H, ArH), 7.33-7.26 (m, 1H, ArH), 7.17-7.07 (m, 5H, ArH), 7.06-6.94 (m, 4H, ArH), 5.29 (s, 2H, CH_2), 3.65 (s, 3H, OCH_3), 2.35 (s, 3H, CH_3); ¹³C-NMR (100 MH_Z, CDCl_3-d_1) δ (ppm): 157.5, 152.8, 145.2, 143.1, 135.2, 134.9, 133.3, 132.4, 132.4, 132.2, 129.9, 129.9, 128.8, 128.3, 126.7, 126.7, 125.3, 124.6, 123.6, 123.3, 121.2, 119.5, 118.9, 117.3, 114.0, 111.2, 111.2, 55.5, 41.0, 21.6; ESI: m/z 543 (M+1)⁺.

Example 29

Synthesis of 2-(4-chlorophenyl)-5-methyl-1-((1-tosyl-indol-3-yl)methyl)benzimidazole (Compound 119)

Compound 119 was prepared in a manner similar to that described in Example 1.
¹H-NMR (200 MH_Z, CDCl_3-d_1) δ (ppm): 8.08 (d, J=8 Hz, 1H, ArH), 7.22-7.62 (m, 5H, ArH), 7.47-7.37 (m, 3H, ArH), 7.35-7.26 (m, 3H, ArH), 7.20-7.18 (m, 2H, ArH), 7.14 (d, J=1 Hz, 1H, ArH), 5.45 (d, J=1 Hz, 2H, CH_2), 2.49 (s, 3H, CH_3), 2.34 (s, 3H, CH_3); ¹³C-NMR (50 MH_Z, CDCl_3-d_1) δ (ppm): 151.7, 145.2, 141.6, 136.7, 135.6, 134.7, 133.5, 130.4, 130.4, 129.9, 129.9, 129.9, 129.2, 129.2, 128.2, 127.2, 127.2, 126.7, 125.6, 125.4, 124.0, 123.7, 119.3, 118.1, 118.9, 114.2, 109.9, 41.5, 21.6, 21.6; ESI: m/z 549 (M+23)⁺.

Example 30

Synthesis of 2-(3-chlorophenyl)-5-methyl-1-((1-tosyl-indol-3-yl)methyl)benzimidazole (Compound 120)

Compound 120 was prepared in a manner similar to that described in Example 1.
¹H-NMR (200 MH_Z, CDCl_3-d_1) δ (ppm): 7.99 (d, J=8 Hz, 1H, ArH), 7.69-7.66 (m, 2H, ArH), 7.58 (d, J=8 Hz, 3H, ArH), 7.52-7.39 (m, 3H, ArH), 7.35-7.29 (m, 2H, ArH), 7.20-7.13 (m, 3H, ArH), 7.08 (s, 2H, ArH), 5.44 (s, 2H, CH_2), 2.50 (s, 3H, CH_3), 2.22 (s, 3H, CH_3); ¹³C-NMR (50 MH_Z, CDCl_3-d_1) δ (ppm): 151.9, 145.1, 143.0, 135.5, 134.9, 134.6, 132.8, 132.2, 131.5, 130.0, 130.0, 129.8, 129.8, 129.2, 128.3, 126.8, 126.8, 126.6, 125.5, 125.0, 124.0, 123.6, 119.9, 118.9, 118.4, 114.1, 109.8, 41.2, 21.5, 21.5; ESI: m/z 526 (M+1)⁺.

Example 31

Synthesis of 5-methyl-2-(4-methylphenyl)-1-((1-tosyl-indol-3-yl)methyl)benzimidazole (Compound 121)

Compound 121 was prepared in a manner similar to that described in Example 1.
¹H-NMR (200 MH_Z, CDCl_3-d_1) δ (ppm): 8.00 (d, J=8 Hz, 1H, ArH), 7.65-7.53 (m, 6H, ArH), 7.38-7.34 (m, 1H, ArH), 7.24-7.14 (m, 6H, ArH), 7.03 (s, 2H, ArH), 5.44 (s, 2H, CH_2), 2.49 (s, 3H, CH_3), 2.37 (s, 3H, CH_3), 2.33 (s, 3H, CH_3); ¹³C-NMR (50 MH_Z, CDCl_3-d_1) δ (ppm): 153.6, 145.0, 142.7, 140.3, 135.6, 134.7, 133.6, 132.7, 129.8, 129.8, 129.6, 129.6, 128.9, 128.9, 128.5, 126.7, 126.7, 126.5, 125.4, 124.6, 124.0, 123.6, 119.6, 119.0, 118.6, 114.1, 109.7, 41.3, 22.0, 21.6, 21.4; ESI: m/z 506 (M+1)⁺.

Example 32

Synthesis of 5-methyl-2-(2-methyphenyl)-1-((1-tosyl-indol-3-yl)methyl)benzimidazole (Compound 122)

Compound 122 was prepared in a manner similar to that described in Example 1.
¹H-NMR (200 MH_Z, CDCl_3-d_1) δ (ppm): 7.93 (d, J=8 Hz, 1H, ArH), 7.58 (d, J=8 Hz, 2H, ArH), 7.47-7.32 (m, 3H, ArH), 7.30-7.24 (m, 2H, ArH), 7.18-7.07 (m, 6H, ArH), 7.02-7.00 (m, 2H, ArH), 5.24 (s, 2H, CH_2), 2.47 (s, 3H, CH_3), 2.33 (s, 3H, CH_3), 2.09 (s, 3H, CH_3); ¹³C-NMR (50 MH_Z, CDCl_3-d_1) δ (ppm): 153.2, 151.0, 145.0, 138.1, 134.7, 132.2, 130.6, 130.1, 130.1, 130.0, 129.8, 129.8, 129.4, 128.6, 126.7, 126.7, 125.9, 125.7, 125.2, 124.4, 124.1, 123.4, 119.6, 118.9, 117.8, 113.8, 109.8, 40.0, 21.5, 21.5, 19.6; ESI: m/z 506 (M+1)⁺.

Example 33

Synthesis of 5-methyl-2-(2-methyphenyl)-1-((1-tosyl-indol-3-yl)methyl)benzimidazole (Compound 123)

Compound 123 was prepared in a manner similar to that described in Example 1.

¹H-NMR (200 MH_Z, CDCl₃-d₁) δ (ppm): 8.00 (d, J=8 Hz, 1H, ArH), 7.67 (s, 1H, ArH), 7.60-7.56 (m, 2H, ArH), 7.52 (s, 1H, ArH), 7.41-7.33 (m, 2H, ArH), 7.31-7.22 (m, 4H, ArH), 7.19-7.12 (m, 4H, ArH), 7.05 (s, 2H, ArH), 5.46 (s, 2H, CH₂), 2.50 (s, 3H, CH₃), 2.32 (s, 3H, CH₃), 2.20 (s, 3H, CH₃); ESI: m/z 506 (M+1)⁺.

Example 34

Synthesis of 2-(2-chlorophenyl)-5-methyl-1-((1-tosyl-indol-3-yl)methyl)benzimidazole (Compound 124)

Compound 124 was prepared in a manner similar to that described in Example 1.
¹H-NMR (200 MH_Z, CDCl₃-d₁) δ (ppm): 7.91 (d, J=8 Hz, 1H, ArH), 7.67-7.57 (m, 3H, ArH), 7.51-7.38 (m, 3H, ArH), 7.31-7.22 (m, 2H, ArH), 7.18-7.12 (m, 2H, ArH), 7.14-7.03 (m, 5H, ArH), 5.31 (s, 2H, CH₂), 2.49 (s, 3H, CH₃), 2.33 (s, 3H, CH₃); ESI: m/z 526 (M+1)⁺.

Example 35

Synthesis of 5-carbonitrile-2-phenyl-3-((1-tosyl-1H-indol-3-yl)methyl) Benzimidazole (Compound 125)

Compound 125 was prepared in a manner similar to that described in Example 1.
¹H-NMR (400 MH_Z, CDCl₃-d₁) δ (ppm): 8.04 (d, J=8 Hz, 1H, ArH), 7.97 (d, J=8 Hz, 1H, ArH), 7.76-7.75 (m, 2H, ArH), 7.60-7.54 (m, 5H, ArH), 7.48-7.37 (m, 4H, ArH), 7.26-7.24 (m, 3H, ArH), 7.16 (s, 1H, ArH), 5.56 (s, 2H, CH₂), 2.37 (s, 3H. CH₃); ESI: m/z 503 (M+1)⁺.

Example 36

Synthesis of 2-(2-fluorophenyl)-5-methyl-1-((1-tosyl-indol-3-yl)methyl)benzimidazole (Compound 126)

Compound 126 was prepared in a manner similar to that described in Example 1.
¹H-NMR (400 MH_Z, CDCl₃-d₁) δ (ppm): 7.91 (d, J=8 Hz, 1H, ArH), 7.65 (s, 1H, ArH), 7.62-7.57 (m, 3H, ArH), 7.48-7.44 (m, 2H, ArH), 7.28-7.19 (m, 1H, ArH), 7.17-7.14 (m, 4H, ArH), 7.11-7.08 (m, 2H, ArH), 7.08 (s, 1H, ArH), 7.01-6.99 (m, 1H, ArH), 5.36 (s, 2H, CH₂), 2.47 (s, 3H, CH₃), 2.32 (s, 3H, CH₃); ¹³C-NMR (100 MH_Z, CDCl₃-d₁) δ (ppm): 161.5, 161.3, 158.8, 148.4, 145.0, 143.2, 142.7, 135.1, 134.7, 133.0, 132.7, 132.4, 132.2, 129.9, 129.8, 128.6, 126.7, 125.2, 124.9, 124.8, 124.4, 123.5, 119.7, 118.8, 117.4, 113.8, 110.1, 408, 21.5, 21.5; ESI: m/z 510 (M+1)⁺.

Example 37

Synthesis of 5-methyl-2-phenyl-1-((1-phenylsulfonyl-indol-3-yl)methyl)benzimidazole (Compound 127)

Compound 127 was prepared in a manner similar to that described in Example 1.
¹H-NMR (200 MH_Z, CDCl₃-d₁) δ (ppm): 8.02 (d, J=8 Hz, 1H, ArH), 7.78 (s, 1H, ArH), 7.74-7.70 (m, 4H, ArH), 7.58-7.50 (m, 2H, ArH), 7.48-7.46 (m, 2H, ArH), 7.42-7.32 (m, 5H, ArH), 7.22 (s, 2H, ArH), 7.19 (d, J=7 Hz, 2H, ArH), 7.11 (s, 2H, ArH), 5.52 (s, 2H, CH₂), 2.49 (s, 3H, CH₃); ¹³C-NMR (50 MH_Z, CDCl₃-d₁) δ (ppm): 152.4, 137.6, 135.5, 134.0, 134.0, 132.8, 130.9, 129.3, 129.3, 129.3, 129.3, 129.1, 129.1, 129.1, 128.3, 127.6, 126.7, 126.7, 126.7, 125.7, 125.7, 124.1, 123.8, 118.9, 118.0, 114.1, 110.1, 41.7, 21.6; ESI: m/z 478 (M+1)⁺.

Example 38

Synthesis of 5-methyl-2-phenyl-1-((1-methylsulfonyl-indol-3-yl)methyl)benzimidazole (Compound 128)

Compound 128 was prepared in a manner similar to that described in Example 1.
¹H-NMR (200 MH_Z, CDCl₃-d₁) δ (ppm): 7.87 (d, J=8 Hz, 1H, ArH), 7.27-7.66 (m, 2H, ArH), 7.64 (d, J=1 Hz, 1H, ArH), 7.45-7.44 (m, 2H, ArH), 7.43-7.37 (m, 2H, ArH), 7.34-7.28 (m, 2H, ArH), 7.24-7.17 (m, 1H, ArH), 7.09 (d, J=1 Hz, ArH), 7.04 (s, 1H, ArH), 5.51 (s, 2H, CH₂), 2.97 (s, 3H, CH₃), 2.47 (s, 3H, CH₃); ¹³C-NMR (50 MH_Z, CDCl₃-d₁) δ (ppm): 153.4, 143.0, 135.2, 133.7, 132.6, 130.0, 129.8, 129.0, 129.0, 128.8, 128.8, 128.3, 125.6, 124.7, 123.7, 123.7, 119.7, 119.2, 117.9, 113.3, 109.6, 40.9, 40.7, 21.5; ESI: m/z 416 (M+1)⁺.

Example 39

Synthesis of 2-(furan-2-yl)-5-methyl-1-((1-tosyl-indol-3-yl)methyl)benzimidazole (Compound 129)

Compound 129 was prepared in a manner similar to that described in Example 1.
¹H-NMR (200 MH_Z, CDCl₃-d₁) δ (ppm): 7.94 (d, J=8 Hz, 1H, ArH), 7.60-7.51 (m, 4H, ArH), 7.36-7.31 (m, 2H, ArH), 7.21-7.12 (m, 5H, ArH), 7.07-7.02 (m, 2H, ArH), 6.54-6.52 (m, 1H, ArH), 5.72 (S, 2H, CH₂), 2.47 (s, 3H, CH₃), 2.30 (s, 3H, CH₃); ESI: m/z 482 (M+1)⁺.

Example 40

Synthesis of 5-methyl-2-(thiophen-2-yl)-1-((1-tosyl-indol-3-yl)methyl)benzimidazole (Compound 130)

Compound 130 was prepared in a manner similar to that described in Example 1.
¹H-NMR (200 MH_Z, CDCl₃-d₁) δ (ppm): 8.03-7.99 (m, 1H, ArH), 7.90-7.86 (m, 1H, ArH), 7.54 (d, J=8 Hz, ArH), 7.48-7.37 (m, 3H, ArH), 7.35-7.21 (m, 5H, ArH), 7.10 (d, J=8 Hz, 3H, ArH), 7.03-6.97 (m, 1H, ArH), 5.61 (s, 2H, CH₂), 2.31 (s, 3H, CH₃); ESI: m/z 484 (M+1)⁺.

Example 41

Synthesis of 2-(furan-2-yl)-1-((1-tosyl-indol-3-yl)methyl)benzimidazole (Compound 131)

Compound 131 was prepared in a manner similar to that described in Example 1.
¹H-NMR (200 MH_Z, CDCl₃-d₁) δ (ppm): 7.94 (d, J=8 Hz, 1H, ArH), 7.86 (d, J=8 Hz, 1H, ArH), 7.53 (d, J=8 Hz, 3H, ArH), 7.35-7.24 (m, 5H, ArH), 7.21-7.18 (m, 2H, ArH), 7.14-7.08 (m, 2H, ArH), 6.57 (dd, J=3, 2 Hz, 1H, ArH), 5.78 (s, 2H, CH₂), 2.30 (s, 3H, CH₃); ¹³C-NMR (100 MH_Z, CDCl₃-d₁) δ (ppm): 145.0, 144.5, 144.2, 143.4, 135.4, 135.0, 134.7, 129.8, 129.8, 129.8, 128.7, 126.7, 126.7, 126.7, 125.3, 124.3, 123.7, 123.6, 119.5, 119.0, 117.9, 114.3, 114.1, 112.3, 110.0, 41.0, 21.5; ESI: m/z 468 (M+1)⁺.

Example 42

Synthesis of 2-(4-(diethylamino)phenyl)-1-((1-tosyl-indol-3-yl)methyl)benzimidazole (Compound 132)

Compound 132 was prepared in a manner similar to that described in Example 1.

$^1$H-NMR (400 MH$_Z$, CDCl$_3$-d$_1$) δ (ppm): 8.19 (d, J=8 Hz, 1H, ArH), 7.76-7.68 (m, 2H, ArH), 7.63 (d, J=8 Hz, 1H, ArH), 7.60-7.56 (m, 2H, ArH), 7.48-7.33 (m, 5H, ArH), 7.26-7.25 (m, 1H, ArH), 7.24-7.19 (m, 2H, ArH), 7.10 (d, J=8 Hz, 1H, ArH), 7.05-7.01 (m, 1H, ArH), 6.72 (s, 1H, ArH), 3.45 (q, J=7 Hz, 4H, NCH$_2$CH$_3$), 2.33 (s, 3H, CH$_3$), 1.24 (t, J=7 Hz, NCH$_2$CH$_3$); ESI: m/z 599 (M+1)$^+$.

Example 43

Effects on Cell Proliferation and Cell Cycle Progression

Anticancer activities of the benzimidazole compounds were evaluated by testing their effects on mammalian cancer cell proliferation and cell cycle progression.

i) SRB Assay

NCI/ADR-RES cell line was obtained from DTP Human Tumor Cell Line Screen (Developmental Therapeutics Program, NCI). Other cancer cell lines (A549, Hep G2, Hep 3B, DU-145, LNCaP, and PC-3) were obtained from American Type Culture Collection (Rockville, Md.). These cancer cells were cultured in RPMI1640 medium with 10% (v/v) fetal bovine serum (FBS) and penicillin (100 units/mL)/streptomycin (100 µg/mL). Cultures were maintained in a humidified incubator at 37° C. in 5% CO$_2$/95% air.

Cells were seeded in 96-well plates in medium with 5% FBS for 24 hrs. They were then further incubated with a vehicle (0.1% DMSO) as control or a test compound for 48 hrs or 72 hrs. The control- or compound-treated cells were fixed with 10% TCA and stained with SRB at 0.4% (w/v) in 1% acetic acid. Unbound SRB was washed off by 1% acetic acid and SRB-bound cells were solubilized with 10 mM Trizma base.

Using an absorbance (515 nm) measurement, the amounts of cellular proteins indicating cell numbers at time zero (T$_0$), in control (C), and in the presence of the test compound (Tx) were obtained. The percentage growth was calculated at each of the compound concentration levels. Percentage growth inhibition was calculated as: 100−[(Tx−T$_0$)/(C−T$_0$)]×100. Growth inhibition of 50% (IC$_{50}$) by a test compound is defined as the concentration of the compound that results in 50% reduction of total protein amount in the control-treated cells.

Compounds 1-63, 68-77, 88-93, 107-114, and 129 were tested. Unexpectedly, among the tested compounds, 23 of them have an IC$_{50}$ value lower than 10 µM in human non-small cell lung cancer A549 cells; 10 of them have an IC$_{50}$ value lower than 10 µM in hepatocellular carcinoma HepG2 cells, 10 of them have an IC$_{50}$ value lower than 10 µM in hepatocellular carcinoma Hep3B cells, and 42 of them have an IC$_{50}$ value lower than 20 µM (among which 20 have an IC$_{50}$ value lower than 10 µM) in prostate cancer PC-3 cells. Also unexpectedly, the IC$_{50}$ values of Compound 55 are 2.4, 3.3, 2.4, 2.3, 2.3, 1.7 and 3.7 µM in A549, HepG2, Hep3B, PC-3, DU-145, LNCaP, and P-glycoprotein (P-gp)-rich breast cancer NCI/ADR-RES cells, respectively.

ii) FACScan Flow Cytometric Analysis

PC-3 cells were treated with Compound 55 (at different concentrations: 1 µM, 3 µM, and 10 µM) for 0 hr, 6 hrs, 12 hrs, 18 hrs, 24 hrs, 36 hrs, and 48 hrs. After treatment, cells were washed twice with ice-cold PBS, collected by centrifugation and fixed in 70% (v/v) ethanol at 4° C. for 30 min. Then, cells were treated with 0.2 ml of a buffer (containing 0.2 M Na$_2$HPO$_4$ and 0.1 M citric acid buffer, pH 7.8) for 30 min, centrifuged, and then incubated in 1 mL propidium iodide (PI) staining buffer (0.1% Triton X-100, 100 µg/mL RNase A, 80 µg/mL propidium iodide in PBS) at 37° C. for 30 min. Cells were detected using a cytofluorometer, and analyzed by FACScan and CellQuest program (Becton Dickinson).

Unexpectedly, Compound 55 induced an increase of cell population at G2/M phase, which was followed by a subsequent increase of hypodiploid (sub-G1, apoptosis) population of the cell cycle.

iii) Western Blotting Analysis on Expression/Activation of Cell-Cycle Regulators PC-3 cells were incubated with a vehicle (0.1% DMSO) as control or Coumpound 55 (10 µM) for 30 min, 45 min, 60 min, and 120 min for testing Ras; or for 6 hrs, 12 hrs, 18 hrs, and 24 hrs for testing Raf-1, Phospho-MEK, MEK, and GAPDH. After the treatment, cells were washed twice with ice-cold PBS and then lysed with 100 µL lysis buffer (20 mM Tris, pH 7.5, 1 mM MgCl$_2$, 125 mM NaCl, 1% Triton X-100, 1 mM phenylmethylsulphonylfluoride, 10 µg/mL leupeptin, 10 µg/mL aprotinin, 25 mM β-glycerophosphate, 50 mM NaF, and 100 µM sodium orthovanadate). Then, the expressions of the above proteins were detected by Western blotting. Unexpectedly, the results indicated that Compound 55 upregulated Ras, Raf-1, and MEK.

The cell-cycle regulators were also examined by Western blot analysis. Proteins in the lysis (40 µg) were separated by electrophoresis in a 10 or 15% polyacrylamide gel, transferred to a nitrocellulose membrane and immuno-reacted with respective antibodies against Cyclin E, Cyclin A, Cyclin B1, Cdk1, Cdk2, p27, MPM2, and GAPDH. The results demonstrated that Compound 55 upregulated cyclin B1 and downregulated cyclin E and cyclin A. Furthermore, the expression of p27 (a Cdk inhibitor) was also decreased by Compound 55. These data suggested that Compound 55 induced the Cdk1 activation and mitotic arrest of PC-3 cells.

Example 44

Inhibition of Tubulin Polymerization i) In Vitro Tubulin Turbidity Assay

Effects of the benzimidazole compounds on tubulin polymerization were detected using CytoDYNAMIX Screen 03 kit (Cytoskeleton, Inc., Denver, Colo.).

Tubulin proteins (>99% purity) were suspended in G-PEM buffer containing 80 mM PIPES, 2 mM MgCl$_2$, 0.5 mM EDTA, and 1.0 mM GTP (pH 6.9) and 5% glycerol with or without a test compound. Then, the mixture was transferred to a 96-well plate and the absorbance was measured at 340 nm (37° C.) for 60 min (SpectraMAX Plus, Molecular Devices Inc., Sunnyvale, Calif.).

Level of tubulin polymerization was determined by examining turbidity of the tubulin suspension. Absorbance of the suspension at 340 nm was plotted as a function of time. Accordingly, the velocity and magnitude of tubulin polymerization were determined.

Compound 55 was tested. Unexpectedly, Compound 55 inhibited tubulin polymerization in a dose-dependent manner.

ii) In Situ Tubulin Assay

The organization and formation of microtubule were detected by immunofluorescence microscopic examination in PC-3 cells.

PC-3 cells were seeded in 8-well chamber slides and incubated with a vehicle (0.1% DMSO, control), Compound 55 (10 μM), taxol (0.1 μM), or vincristine (0.1 μM) for 18 to 24 h. Then, the cells were fixed with 100% methanol at −20° C. for 5 min and incubated in 1% bovine serum albumin (BSA) containing 0.1% Triton X-100 at 37° C. for 30 min. Cells were then washed twice with PBS for 5 min and stained with primary antibody specific to β-tubulin at 37° C. for 1 h. Afterwards, FITC-labeled secondary antibodies were used (staining performed at 37° C. for 40 min, green fluorescence) and the protein was detected using a confocal laser microscopic system (Leica TCS SP2). The nuclei were visible by DAPI staining (1 mg/mL DAPI, blue fluorescence).

The in situ labeling of tubulin and chromosomes demonstrated that multi-polar spindles and multiple nuclei were formed in taxol-treated cells while multi-polar spindles and chromosome condensation were observed in vincristine-treated cells. Differently and unexpectedly, the major spindles formed in Compound 55-treated cells were monopolar.

Example 45

Effect on Inducing Apoptosis

Effect of benzimidazole compounds on inducing apoptosis was evaluated by testing their effect on the expression/activation of Bcl-2 family member proteins, caspases, and c-Jun N-terminal kinase (JNK). Bcl-2 family of proteins is the most important regulators of mitochondria-involved apoptotic cell death. The pro-apoptotic members, Bax, Bak and Bad, are required for the disruption of mitochondria; whereas the anti-apoptotic Bcl-2, Bcl-xL and Mcl-1 can prevent apoptosis by antagonizing the pro-apoptotic members.

PC-3 cells were incubated with a vehicle (0.1% DMSO) or Compound 55 (10 μM) for 0 hr, 6 hrs, 12 hrs, 18 hrs, 24 hrs, and 36 hrs. Then, the cells were harvested and lysed for the detection of protein expression with specific antibodies by western blot analysis. For Western blotting, the proteins (40 μg) in the lysis (including Phospho-Bcl-2, Bcl-2, Phospho-Bcl-xL, Bcl-xL, Mcl-1, Bax, Bak, Bad, GAPDH, cleaved Bad, Caspase-9, cleaved Caspase-9, Caspase-3, cleaved Caspase-3, poly-(ADP-ribose) polymerase (PARP), cleaved PARP, and GAPDH) were separated by electrophoresis in a 10 to 15% polyacrylamide gel, transferred to a nitrocellulose membrane and immuno-reacted with specific antibodies.

Both anti-apoptotic and pro-apoptotic members of Bcl-2 family were detected and the results show that Compound 55 unexpectedly induced the phosphorylation and degradation of Bcl-2 and Bcl-xL, and the decrease of Mcl-1 expression. In addition, the cleavage of pro-apoptotic Bad into 15-kDa fragments was unexpectedly induced by Compound 55. This suggested that Compound 55 triggered apoptosis of PC-3 cells. Next, levels of various caspases in Compound 55-treated cells were determined by Western blot analysis. The results show that caspase-9, caspase-3 and PARP were cleaved to produce catalytically active fragments, suggesting the activation of these caspases.

Further, effects of benzimidazole compounds on JNK activation were evaluated. PC-3 cells were treated with a vehicle (0.1% DMSO), Compound 55 (10 μM) or a mixture of Compound 55 and SP600125 (20 μM, a specific JNK inhibitor) for 12 hrs, 24 hrs, and 36 hrs. Then, the cells were fixed and stained with propidium iodide to analyze DNA content by FACScan flow cytometer.

The results show that SP600125 significantly inhibited apoptosis induced by Compound 55 in PC-3 cells, indicating Compound 55-induced apoptosis is mediated by JNK. Also, the SP600125-reversible cell population was shifted to G2/M phase of the cell cycle, indicating that JNK-mediated apoptosis occurred after the checkpoint arrest at G2/M phase.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

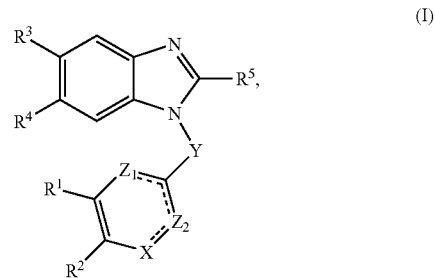

wherein
each - - - is a single bond or a double bond, provided that if one - - - is a double bond, its neighboring - - - is not a double bond;
X is CR' and each of $Z_1$ and $Z_2$ is CH;
Y is $CH_2$;
each of R', $R^1$ and $R^2$ is methoxy;
$R^3$ is a monovalent nonaromatic 5-8 membered monocyclic ring system having one or more heteroatoms selected from the group consisting of N and O;
$R^4$ is H, alkyl, or halo;
$R^5$ is aryl, or heteroaryl;
or a salt, or a prodrug thereof.

2. The compound of claim 1, wherein $R^5$ is phenyl or furyl.

3. The compound of claim 1, wherein the compound is 2-phenyl-5-(pyrrolidin-1-yl)-1-(3,4,5-trimethoxybenzyl)-1H-benzo[d]imidazole.

4. A pharmaceutical composition, comprising a compound of claim 1 and a pharmaceutically acceptable carrier.

5. The compound of claim 1, wherein the compound is 2-(furyl)-5-(pyrrolidinyl)-1-(3,4,5-trimethoxybenzyl)benzimidazole.

6. A method for inhibiting growth of cancer cells in vitro, comprising treating the cancer cells with an effective amount of a compound of claim 1 and a pharmaceutically acceptable carrier.

7. The method of claim 6, wherein $R^5$ is phenyl or furyl.

8. The method of claim 6, wherein $R^3$ is piperazinyl, pyrrolidinyl, dioxanyl, morpholinyl or tetrahydrofuranyl.

9. The method of claim 6, wherein $R^3$ is pyrrolidinyl.

10. The method of claim 6, wherein the compound is 2-phenyl-5-(pyrrolidin-1-yl)-1-(3,4,5-trimethoxybenzyl)-1H-benzo[d]imidazole, or 2-(furyl)-5-(pyrrolidinyl)-1-(3,4,5-trimethoxybenzyl)benzimidazole.

11. The method of claim 6, wherein the cancer cells are human non-small cell lung cancer cells, human hepatocellular carcinoma cells or human prostate cancer cells.

12. The compound of claim 1, wherein $R^3$ is piperazinyl, pyrrolidinyl, dioxanyl, morpholinyl or tetrahydrofuranyl.

13. The compound of claim 1, wherein $R^3$ is pyrrolidinyl.

* * * * *